Figure 1:
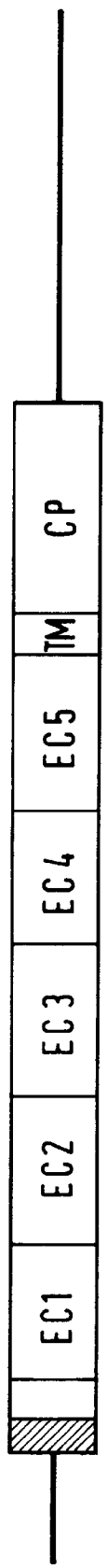

United States Patent [19]
Takeshita et al.

[11] Patent Number: 5,869,638
[45] Date of Patent: Feb. 9, 1999

[54] BONE-RELATED CADHERIN-LIKE PROTEIN AND PROCESS FOR ITS PRODUCTION

[75] Inventors: Sunao Takeshita, Tokorozawa; Makoto Okazaki, Kawagoe; Shinji Kawai, Fujimi; Atsushi Tsujimura, Muko; Egon Amann, Tokyo, all of Japan

[73] Assignee: Hoechst Japan Limited, Tokyo, Japan

[21] Appl. No.: 738,349

[22] Filed: Oct. 25, 1996

Related U.S. Application Data

[63] Continuation of Ser. No. 364,439, Dec. 27, 1994, abandoned, which is a continuation of Ser. No. 112,061, Aug. 26, 1993, abandoned.

[30] Foreign Application Priority Data

Aug. 28, 1992 [JP] Japan .................................. 4-230028

[51] Int. Cl.⁶ .......................... C07H 21/02; C07H 21/04
[52] U.S. Cl. ...................... 536/23.5; 536/23.4; 435/69.1; 435/69.7; 435/325; 435/255.1; 435/252.3; 435/252.33
[58] Field of Search .................. 536/23.5, 23.4; 435/69.1, 69.7, 325, 255.1, 252.3, 252.33, 320.1

[56] References Cited

U.S. PATENT DOCUMENTS 5,639,634  6/1997  Suzuki .

FOREIGN PATENT DOCUMENTS

WO 92/00324  1/1992  WIPO .
WO 93/00353  1/1993  WIPO .

OTHER PUBLICATIONS

Takamatus et al., Biochem. and Biophysical Research Communications, 185 (1): 224–230 (May 29, 1992).
Tezuka et al., Biochem. and Biophysical Research Communications, 173 (1) 246–251 (Nov. 30, 1990).
Boyle et al., Genomics, 12:517–525 (1992).
"Contact and Adhesive Specificities in the Associations, Migrations, and Targeting of Cells and Axons", Hynes et al., Cell, 68:303–322 (1992).
"Cadherin Cell Adhesion Receptors as a Morphogenetic Regulator", Masatoshi Takeichi, Science, 251:1451–1455 (1991).
Ranscht, B. et al., *Neuron*, 7:391–402, 1991.
Ranscht, b et al., Medline Abstract, Accession No. 92000685 for *Neuron* 7(3): 391–402, 1991.
Merck Manual 16th Edition, Berkow et al. (eds.), Merck Research Labortories; Rahway, N.J., 1992, pp. 1357–1360.

*Primary Examiner*—Paula K. Hutzell
*Assistant Examiner*—Heather A. Bakalayar
*Attorney, Agent, or Firm*—Finnegan, Henderson, Farabow, Garrett & Dunner, L.L.P.

[57] ABSTRACT

A bone-related protein named OSF-4 which is obtained from bone tissue of a mammal including mouse or human, and a process for its production. This protein is a novel naturally occurring mammal protein of the cadherin family.

OSF-4 acts as an adhesion molecule or a growth factor which takes part in the process of osteogenesis at the site of bone induction. OSF-4 can be used as an agent for treating bone metabolic diseases, and its high organ specificity for bones enables its use as a diagnostic reagent for bone metabolic diseases.

6 Claims, 4 Drawing Sheets

1   THYMUS
2   SPLEEN
3   BRAIN
4   KIDNEY
5   LIVER
6   LUNG
7   TESTIS
8   HEART
9   OSTEOBLAST-ENRICHED CELL FROM MOUSE CALVARIA
10  MC3T3-E1 CELLS FROM 3 DAYS CULTURE
11  MC3T3-E1 CELLS FROM 12 DAYS CULTURE
12  MC3T3-E1 CELLS FROM 60 DAYS CULTURE
13  NIH3T3 CELLS

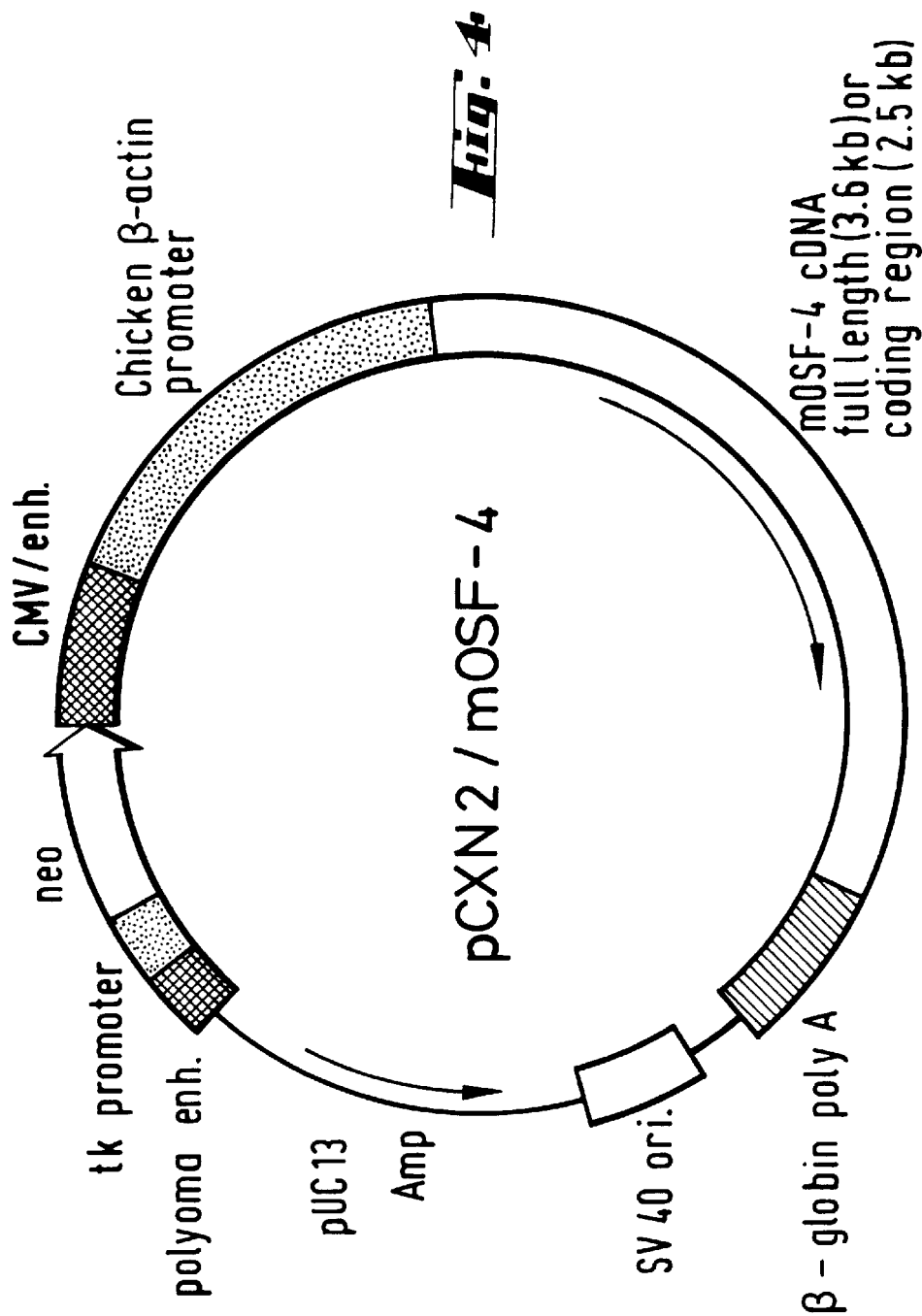

BONE-RELATED CADHERIN-LIKE PROTEIN AND PROCESS FOR ITS PRODUCTION

This is a continuation of application Ser. No. 08/364,439, filed Dec. 27,1994, now abandoned which is a continuation of application Ser. No. 08/112,061, filed Aug. 26, 1993, now abandoned.

This invention provides a novel bone-related protein. It is named OSF-4 and belongs to a group of cadherin molecules. The OSF-4 can be obtained from bone tissue of a mammal including mouse or human. This bone-related protein is useful for the diagnosis and treatment of bone metabolic diseases.

Bone metabolic diseases include osteoporosis, Paget's disease, osteomalacia, hyperostosis, and osteopetrosis. Osteoporosis, in particular, has a high incidence enough to affect about more than a half of postmenopausal women and elderly people, and effective methods for its diagnosis and treatment have been strongly desired.

Bone metabolic diseases involve some disorder of bone metabolism at the cellular level in bone tissue. The discovery, isolation and identification of factors associated specifically with bone metabolism are very effective for elucidating this disorder.

A cell line of osteoblasts which play a major role in osteogenesis, has been used and a proteinaceous factor produced specifically by this cell line has been identified. Therefore, the present invention provides a novel protein named OSF-4 which is substantially bone-specific, and which is highly homologous with various known cadherin type cell adhesion molecules in terms of amino acid sequence.

The OSF-4 can also be produced from the DNA sequence described in the present specification by an ordinary genetic engineering technique known in the art. Furthermore, the OSF 4 or its fragment can be produced from the amino acid sequence described in the specification by a chemical peptide synthesis method. Moreover, that fragment of the DNA sequence of the OSF-4 described in the present invention which is specifically different from other cadherin molecules can be synthesized with a length of 15 to 50 bases by an ordinary chemical oligonucleotide synthesis method. That fragmentary sequence can be used as a DNA probe for finding and identifying bone-derived cells. This identification of bone-derived cells is useful particularly for grasping the origin of metastatic or recurrent carcinoma, thus leading to an appropriate therapy for recurrent cancer. Of the partial peptides of the OSF-4, the peptide in the epitope portion that can be recognized by antibodies is usable for preparing a monoclonal antibody specific for the OSF-4. The resulting monoclonal antibody is of marked value for identifying bone-derived cells by an immunological cell tissue staining method. Because of its similarity to cell adhesion molecules, the OSF-4 is also useful for the treatment of fracture.

OSF-4 is a bone-specific cadherin-like proteinaceous factor. The following is known about cadherin which is a cell adhesion molecule involved in morphogenesis.

The segmentation of cell population is one of the most basic elements for the construction of an animal body. This segmentation begins at a very early stage of morphogenesis. As the differentiation of cells proceeds, the same types of cells migrate and become reorganized in an orderly manner, thereby performing morphogenesis as well as the construction and maintenance of tissues. One of the elements that control such cellular migration is the selective adhesion of cells. Cells have the features of recognizing adjacent cells or adjacent extracellular matrices, and adhering to only particular ones. In accordance with the differentiation of cells, their adhesion specificities vary. Consequently, these cells may leave particular sites, migrating to and gathering at the sites where they should have originally been situated. So far, numerous cell adhesion molecules have been identified and all show cell type specificities. These molecules can be roughly classified into more than 4 groups, i.e. cadherin family, immunoglobulin superfamily adhesion molecules, integrin superfamily, selecting, and those not belonging to these categories (Hynes et al., (1992) Cell, vol. 68, pp. 303–322).

Cadherins, in particular, have been well analyzed, and not only their structures, but their functions have also been extensively studied. Cadherins are glycoproteins with molecular weights of about 120 kD, and are $Ca^{2+}$- dependent intercellular adhesion molecules (Takeichi, (1991), Science, vol. 251, pp. 1451–1455). Nearly 10 types of them have been identified. The respective types have binding specificities, and the same molecules react homophilically with each other. As a result, cells having the same type of cadherin bind selectively to each other. Thus, cadherins are considered indispensable for determining the specificities of intercellular adhesion. Typical examples are E-cadherin (epithelial cadherin), P-cadherin (placental cadherin), N-cadherin (neural cadherin), and L-CAM (liver cell adhesion molecule). All of them are similar in structure; each is composed of an extracellular region comprising 4 to 5 repeats of about 110 amino acids, a transmembrane region, and a cytoplasmic region comprising about 150 amino acids. Comparisons among the respective subclasses have shown about 50% identity of the amino acids. In the extracellular region, the identity rate is higher at a site nearer the N-terminus; it becomes gradually lower the nearer the transmembrane region; and it is maximal in the cytoplasmic region. In recent years, new cadherins have been reported, including, for instance, M-cadherin (muscle cadherin), B-cadherin (brain cadherin), T-cadherin (truncated cadherin), and desmoglein localized in desmosomes. These cadherins may originate from a single ancestor gene, and constitute the cadherin family.

Close studies of a cadherin molecule have shown that sites binding to calcium ions and sites determining binding specificity are present in its N-terminal region. The cytoplasmic domain has been found to be functionally important for the adhesion property, and to bind to a protein such as catenin or actin. Through these functions, cadherins have been suggested to contribute to cytoplasmic signaling. During invasion and metastasis of cancer cells, these cadherins undergo quantitative changes, and so their relationship with oncogenesis has attracted a broad attention. Despite many such reports of cadherin molecules, there have been no reports of cadherin molecules with specificity for osteoblasts.

Bone formation and maintenance are dependent on the balance between osteoblasts which form bones and osteoclasts which resorb bones. Osteoblasts are mesenchymal cells of the same origin as myoblasts and ajpocytes, while osteoclasts originate from stem cells as do neutrophils and macrophages. Osteoclasts are known to express vitronectin receptors which belong to the integrin family. With osteoblasts, the presence of cell adhesion molecules has only been suggested.

The object of the present invention is to find a new type of cell adhesion factor which is specifically expressed in osteoblasts. Such a new cell adhesion factor is an important molecule for the proliferation, differentiation, migration and reorganization of osteoblasts. This substance can be expected to find use in the diagnosis and treatment of various bone metabolic diseases.

cDNA of mouse OSF-4 (mOSF-4) was isolated from a mouse osteoblastic cell line MC3T3-E1 cDNA library constructed by a combination of PCR (polymerase chain reaction) and the subtraction method, and by differential screening. Then, the mouse OSF-4 cDNA was used as a probe for screening cDNA libraries obtained from human osteosarcoma cells. As a result, two types of OSF-4, named hOSF-4-1 and hOSF-4-2, were obtained, and their nucleotide sequences were determined. The nucleotide sequence of the OSF-4 is very well conserved between mouse and human. Comparisons between mOSF-4 and hOSF-4-1 as well as hOSF-4-2 show 97.1% and 96.4% identity in amino acid level, respectively (Tables 1 to 3). The very high conservation between these species suggests that OSF-4 has essential roles in vertebrate bone metabolism. OSF-4 can be isolated and purified from the bone extracts of other vertebrates. The OSF-4 of other animal species can be obtained from cDNA libraries or genomic libraries constructed from their bones, cultured bone cells and other body tissues by recombinant gene technology using the cDNA of the present invention or its DNA fragment as a probe. Search through the currently available DNA and amino acid sequence data bases demonstrated the sequence of the cDNA in the present invention to be novel.

In comparison with the amino acid sequence of mOSF-4, hOSF- 4-1 shows high conservation in the whole domain. hOSF-4-2, on the other hand, is completely identical with hOSF-4-1 in terms of the N-terminal to 631st amino acid residues. Because of the insertion of 179 bases into the transmembrane region, however, frameshift occurs, with the result that the 62 amino acid residues ranging from the 632nd amino acid residue to the 693rd-position C-terminus assume a completely different structure (Tables 1 to 3). Hence, the C-terminal 9 amino acid residues in the transmembrane region, and the cytoplasmic region are completely different between hOSF-4-1 and hOSF-4-2. Such cadherin with the C-terminal region deleted corresponds to T-cadherin. This type of cadherin has been suggested to take part in the control of cell adhesion.

A peptide corresponding to 15 hydrophilic amino acid residues at the 101st to 115th positions in the EC1 domain of mOSF-4 was chemically synthesized. This peptide was conjugated with KLH (keyhole limpet hemacyanin), and used for immunization of rabbits. The resulting anti-mOSF-4 peptide antisera were used for immunohistochemical detection of OSF-4 in systemic slices of the neonatal mouse. OSF-4 was detected in the osteoblasts, chondrocytes and so on.

Generally, the OSF-4 can be directly extracted from bone tissue or cartilage tissue of a human, bovine, murine or other source by a known biochemical technique. The DNA coding for the OSF-4 can be obtained by constructing a cDNA library or a genomic library from mRNA extracted from vertebrate bone tissue, and using a probe comprising a labeled fragment of the mouse DNA sequence disclosed in the present specification. A full length cDNA clone can be obtained by a combination of the above-described and other standard techniques on molecular biology.

As described above, OSF-4 shows homology with known representative cadherin molecules, but it is a cadherin molecule belonging to a new subclass different from those so far reported. Its structure is composed of 5 repeats in an extracellular region, a transmembrane region, and a cytoplasmic region (FIG. 1). Comparisons between OSF-4 and other cadherins have shown that homology in the extracellular region becomes lower from the N-terminus toward the transmembrane region and the highest homology is noted in the cytoplasmic region, according to the homology pattern among the existing different cadherin molecules (Table 4).

TABLE 4

Comparisons of amino acids among mouse OSF-4 and other cadherin molecules

| Types of cadherin compared | Homology (%) | | | | | | | |
|---|---|---|---|---|---|---|---|---|
| | EC1 | EC2 | EC3 | EC4 | EC5 | TM | CP | MP |
| OSF-4:N | 39.3 | 46.8 | 32.8 | 29.8 | 27.4 | 59.4 | 50.3 | 39.4 |
| OSF-4:E | 32.7 | 40.4 | 30.7 | 30.8 | 17.2 | 34.4 | 47.1 | 33.9 |
| OSF-4:P | 34.6 | 35.8 | 36.0 | 29.1 | 19.0 | 23.1 | 43.8 | 33.3 |
| OSF-4:M | 31.8 | 38.5 | 27.6 | 26.0 | 25.4 | 34.4 | 45.1 | 33.2 |
| N:E | 60.2 | 53.5 | 45.1 | 43.9 | 27.0 | 46.9 | 64.1 | 49.8 |
| N:P | 51.9 | 51.8 | 45.1 | 49.5 | 27.9 | 30.8 | 57.7 | 47.3 |
| E:P | 65.7 | 61.1 | 52.7 | 46.7 | 38.9 | 53.8 | 79.7 | 58.7 |

In Table 4, the homology of amino acids in each region was calculated and expressed in %. The abbreviations are as follows: EC1 to EC5, five extracellular regions; TM, transmembrane region; CP, cytoplasmic region; MP, mature protein; N,N-cadherin; E,E-cadherin; P,P-cadherin; and M,M-cadherin. In the column "Types of cadherin compared," OSF-4:N denotes comparisons of the amino acid sequences in the respective regions between OSF-4 and N-cadherin (the same is true for the other combinations).

The protein provided by the present invention is a group of glycoproteins, named OSF-4, which belongs to a new cadherin subclass and plays an important role in osteogenesis. More concretely, the human and mouse OSF-4 proteins described in this specification are included. OSF-4 is expressed in osteoblasts during the process of bone formation, and acts as a cell adhesion molecule and a morphogenesis-related substance. These human and mouse OSF-4 proteins can be used to identify and isolate other mammalian OSF-4 proteins similar in DNA sequence and amino acid sequence.

The present invention further provides polypeptides comprising analogues of OSF-4, i.e. mutants and fused proteins having OSF-5 adinty, as well as fragments of the OSF-4 which can be identified as OSF-4 related, particularly with at least 10, preferably 15 amino acids. The cDNA of mouse OSF-4 isolated from the mouse osteoblastic cell line MC3T3-E1 encodes a protein consisting of 796 amino acids, including a signal peptide composed of 24 amino acid residues. There are two isoforms of human OSF-4 which were isolated from a human osteosarcoma cDNA library. One cDNA clone, human OSF-4-1, encodes a protein consisting of 796 amino acids including a signal peptide composed of 24 amino acid residues. The other cDNA clone, human OSF-4-2, encodes a protein consisting of 693 amino acids including a signal peptide composed of 24 amino acid residues. The present invention also provides a process for producing OSF-4 by recombinant DNA technology.

According to the present application the term "hybridization under stringent conditions means hybridization conditions with a salt concentration of 6×SSC (NaCl-citrate puffer) at 62°–68° C.

BRIEF EXPLANATION OF TABLES AND FIGURES

Table 1 shows an alignment of the amino acid sequences of mouse OSF-4, human OSF-4-1 and human OSF-4-2. Common amino acid residues are shown in the form of consensus.

Table 2 shows a continuation of an alignment of the amino acid sequences of mouse OSF-4, human OSF-4-1 and human OSF-4-2 shown in Table 1. Common amino acid residues are shown in the form of consensus.

Table 3 shows a continuation of an alignment of the amino acid sequences of mouse OSF-4, human OSF-4-1 and human OSF-4-2 shown in Table 2. Common amino acid residues are shown in the form of consensus.

```
ATOS-1/2:
   ATOS-1    5'-    CTCTTGCTTGAATTCGGACTA-3'     SEQ ID NO: 7
   ATOS-2    3'-ACACGAGAACGAACTTAAGCCTGAT-5'     SEQ ID NO: 8

ATOS-4/5:
   ATOS-4    5'-    CTCTTGCTTAAGCTTGGACTA-3'     SEQ ID NO: 9
   ATOS-5    3'-ACACGAGAACGAATTCGAACCTGAT-5'     SEQ ID NO: 10
```

FIG. 1 is a schematic drawing of the structure of mouse OSF-4 precursor protein. OSF-4 precursor protein is divided into eight regions, a signal region (shaded part), five extracellular regions (EC1, EC2, EC3, EC4 and EC5), a transmembrane region (TM) and a cytoplasmic region (CP).

Figure 2:
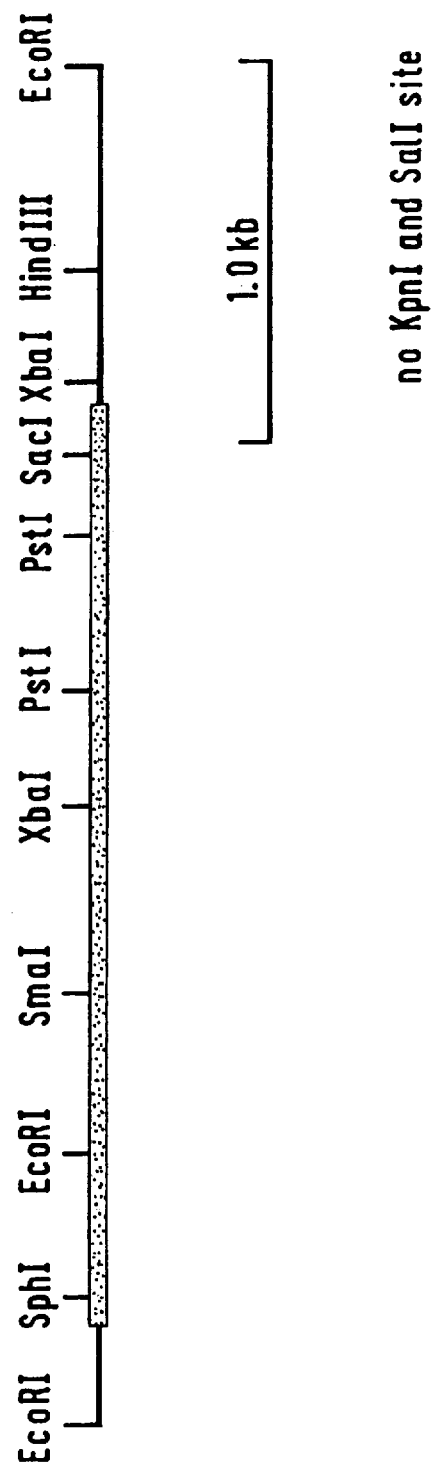

FIG. 2 shows a restriction enzyme map of cDNA coding for mouse OSF-4. The bold letters indicate the region coding for the amino acid of OSF-4. There are no Kpnl and Sall sites in the map.

Figure 3:
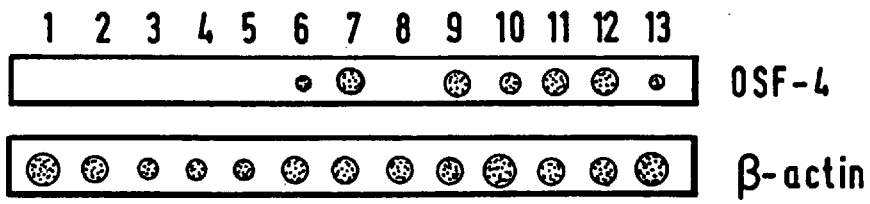

FIG. 3 shows the tissue-specific expression of mouse OSF-4. This was analyzed by purifying RNA from various tissue and cultured cells followed by RNA dot blotting. This diagram shows the results of autoradiography.

FIG. 4 shows the map of expression vector pMSS60. It is mentioned that the content of the Japanese priority application NO. 230028192 is also part of the present application.

EXAMPLES

The present invention will be described in more detail by reference to the following Examples:

Example 1

Construction of cDNA Library by Subtraction and PCR

The construction of a cDNA library specific for the osteoblastic cell line MC3T3-E1 will be hereinafter described. This cDNA library is constructed from MC3T3-E1 cDNA library by a combination of the subtraction method and the PCR with the gene expressed in mouse liver tissue being subtracted. Each cDNA clone has gene fragments with an average length of about 300 bases, and is characterized in that the gene with a low content has been amplified too.

Unless otherwise specified, all general recombinant DNA protocols complied with Sambrook et al., "Molecular Cloning Manual" (1989), Cold Spring Harbor Laboratory, Cold Spring Harbor, U.S.A. Total RNAs were extracted from $8 \times 10^7$ MC3T3-E1 cells and about 1 g of mouse liver tissue by the guanidine method. Poly A$^+$ RNAs were purified from the total RNAs by means of the commercially available product "Oligo dT Latex mRNA Purification Kit" (Takara Shuzo). cDNAs were synthesized by a cDNA synthesis kit (Amersham) using 1 µg of each poly A$^+$ RNA as a template. However, a random primer was used, instead of an oligo dT primer, in an amount of 1.5 times its ordinary amount used, whereby the cDNA chain elongation was restricted to an average length of about 300 bases. After the cDNAs were made double-stranded and blunt-ended by use of the above kit, they were joined with T4DNA ligase (Takara Shuzo) to the following two DNA linkers, i.e. ATOS-1/2(SEQ ID NO. 7 and SEQ ID NO:8 of the Sequence Listing) for the MC3T3-E1 cDNA, and ATOS-4/5 (SEQ ID NO:9 and SEQ ID NO:10 of the Sequence Listing) for the liver cDNA:

Then, each reaction product was subjected to DNA amplification by the PCR (polymerase chain reaction) method using ATOS-1 and ATOS-4, respectively, as primers. The amplified DNA concentration was determined with the DNA assay kit "DNA Dipstick" (Invitrogen). The subtraction method was performed using photobiotin (Pirce). Photobiotin (20 ng) was added to 20 µg of the PCR-amplified liver cDNA, and light from a sunlamp 10 cm apart was projected onto the liver cDNA for 10 minutes to label it with biotin. To 3.0 µg of the labeled liver cDNA was added 0.3 µg of unlabeled MC3T3-E1 cDNA for hybridization. Then, streptavidin (Takara Shuzo) was reacted, and the reaction mixture was extracted with phenol to remove cDNA common to the liver cDNA from the MC3T3-E1 cDNA. The subtraction method was repeated to remove as much of the common cDNA as possible from the MC3T3-E1 cDNA. DNA was amplified by PCR using the aforementioned ATOS-1, and the DNA concentration was measured. This cDNA (10 ng) was digested with the restriction enzyme EcoRI, and then ligated with T4 ligase to 1 µg of the phage vector lambda gt10 (lambda gt10/EcoRI cloning kit, Stratagene) which was digested with EcoRI and dephosphorylated at its ends. The resulting recombinant DNA was packaged into lambda phage particles by use of the in vitro packaging kit "Gigapack-gold" (Stratagene). The recombinant phages were infected into E. coli C600 (preserved as HT003 at Japanese Cancer Research Resources Bank, National Institute of Health of Japan), and the organisms were applied to an agar medium along with a soft agar medium to form phage plaques. The efficiency of infection was determined to be $3 \times 10^6$ phage plaques/µg vector DNA.

The resulting cDNA library was subjected to differential screening to select clones with a high specificity for MC3T3-E1. Concretely, $2.25 \times 10^4$ phages were applied to total 10 plates, and the resulting plaques on each plate were transferred to two nylon membrane filters (total 20 filters). These series of plaques were subjected to plaque hybridization with radiolabeled MC3T3-E1 cDNA as the probe for one of the series, and with radiolabeled liver cDNA for the other series. In 273 clones, expression was observed with the MC3T3-E1 cDNA probe, but not with the liver cDNA probe. These clones were used as a mini-library in subsequent experiments.

Example 2

Isolation of Mouse OSF-4 Clone

A description will be made of methods to identify a cDNA fragment of OSF-4 as an MC3T3-E1 specific clone from the mini-library constructed in Example 1, and to clone full length cDNA from the cDNA library of MC3T3-E1 with the use of this fragment.

The total RNAs from MC3T3-E1 and liver prepared in Example 1 were spotted in an amount of 1 µg each onto nylon membrane filters. 273 of the filters were prepared, and used for hybridization to be described later on. Separately, the DNA of the inserts of the 273 phage clones prepared in Example 1 was amplified by PCR. This DNA was agarose gel electrophoresed, and main bands were cut out, purified, and radiolabeled for use as a probe. A clone showing expression with MC3T3-E1 cDNA but no expression with liver cDNA upon autoradiography was recloned into a plasmid vector. Concretely, the DNA of the inserts amplified by PCR and then purified was digested with the restriction enzyme EcoRI, and recloned into the EcoRI site of the plasmid vector pUC118 (Takara Shuzo). The DNA sequence of the resulting clone was determined with commercially available "DNA Sequence Kit" (Takara Shuzo) using a universal primer, Search through DNA and protein data bases showed that DNA sequence to constitute a clone homologous with the existing cadherin. This clone was designated as D45, and used for subsequent cloning of the full length cDNA.

For cloning of the full length cDNA, blund-ended double-stranded cDNA was synthesized with the cDNA synthesis kit "cDNA Synthesis System Plus" (Amersham) using 5 µg of the poly A$^+$ RNA of MC3T3-E1 purified in Example 1. The resulting cDNA was ligated to EcoRI/NotI adaptor (Takara Shuzo) using T4 ligase, and the product was agarose gel electrophoresed to purify a fragment more than about 700 base pair long. This fragment was joined to the EcoRI site of lambda gt10 phage vector (Stratagene), and packaged into phage particles in the same way as in Example 1. The packages were infected into *E. coli* as in Example 1, and the efficiency of infection was determined to be $1.5 \times 10^7$ phage plaques/µg vector DNA. The aforementioned D45 was radiolabeled for use as a probe, and $1.0 \times 10^6$ phage clones of the cDNA hybridization. Fourteen positive hybridization. Fourteen positive hybridization signals were obtained, whereafter the NotI fragment of the phage clone with the longest insert was recloned into the NotI site of the plasmid vector pGEM11 Zf(+) (Stratagene). The resulting clone was designated as pKOT164.

Example 3

Determination of Mouse OSF-4 DNA Sequence

Deletion mutants of the pKOT164 and a subclone containing its cDNA fragment were prepared with "the Deletion Kit for Kilo Sequence" (Takara Shuzo) by cutting at intervals of about 300 base pairs in each opposite direction. The DNA sequence of each deletion mutant was determined with the automatic DNA sequencer 373A (Applied Biosystems, U.S.A.). The entire DNA sequence of the cDNA, and an amino acid sequence translated from this DNA sequence are shown as SEQ ID NO: 1 of the Sequence Listing. The protein encoded by this cDNA was designated as OSF-4. (SEQ ID NO: 2) No. 1 of the amino acid residue corresponds to the N-terminus of the predicted OSF-4 precursor protein. The restriction enzyme map of that cDNA is shown in FIG. 2.

Example 4

Tissue Specific Expression of Mouse OSF-4

RNA dot blotting was performed to investigate the tissue specific expression of mouse OSF-4. The total RNAs of the thymus, spleen, brain, kidney, liver, lung, testis and heart of mice (purchased from Nippon Clea) were prepared by the guanidine method. Calvarial osteoblast-rich cells were obtained from a culture of newborn mice calvaria. Total RNA was extracted from these cells in the same way as described above. One µg of the total RNA each from the above-mentioned tissues, cultured calvarial cells, MC3T3-E1 and mouse fibroblast cell line NIH3T3 (ATCC CRL 1658) was dotted onto nylon membrane filters (Biodyne, PALL), fixed by baking, and used for hybridization. Separately, the pKOT164 was digested with NotI, and isolated and purified by agarose gel electrophoresis. Then, the isolate was radiolabeled and used as a probe. Autoradiography indicated high expression for the cultured calvarial cells and MC3T3-E1, and low expression for the lung and testis (FIG. 3).

Example 5

Cloning of cDNA Coding for Human OSF-4

The NotI fragment containing the cDNA region of pKOT164 was purified and used as a probe to screen a human osteosarcoma cDNA library consisting of $1.3 \times 10^5$ clones. Twenty-one positive signals were obtained, and 5 clones were isolated. Two clones with large inserts were recloned into plasmid vector pHSG398. The resulting plasmids were designated as pKOT161 and pKOT170.

Example 6

Determination of Human OSF-4 DNA Sequence

From the pKOT161 and pKOT170 cloned in Example 5 and their subclones, deletion mutants were prepared in the same way as in Example 3. Then, their DNA sequences were determined. These DNA sequences and the amino acid sequences predicted from them are shown in SEQ ID NO:3 and SEQ ID NO:5 of the Sequence Listing. The proteins encoded by these cDNAs were designated as human OSF-4(SEQ ID NO: 4) and human OSF-4-2(SEQ ID NO:6) . The amino acid residue No. 1 of each of them corresponds to the N-terminus of the predicted OSF-4 precursor protein.

Example 7

Preparation of Anti-OSF-4 Antisera

In preparing anti-peptide antibodies against mouse OSF-4, the corresponding 15 amino acid residues in the EC1 were synthesized by the solid phase synthesis method using a peptide synthesizer (430A, Applied Biosystems), in accordance with an experimental report on M-cadherin (Donalies et al., (1991), Proc. Natl. Acad. Sci., U.S.A., vol. 88, pp. 8024–8028). The synthetic peptide was OSF-4.1 (FVIDDKSGNIHATKT, SEQ ID No:11 of the Sequence Listing). This synthetic peptide was conjugated with KLH (keyhole limpet hemacyanin) using glutaraldehyde as a coupling agent, and used for immunization of rabbits. The resulting antisera could be used to search immunohistochemically for the presence of OSF-4 in newborn mouse systemic slices, and to detect the expression of OSF-4 in *E. coli*, yeast and animal cells.

Example 8

Expression of OSF-4 in Animal Cells

The present example describes the preparation and expression of the expression vector for mouse OSF-4 in animal cells and the functional analysis of the produced OSF-4.

There is an open-reading frame in the 5'-flanking region of the OSF-4-coding region in the base sequence as shown in SEQ ID NO: 1 in Sequence Listing. The open-reading frame was expected to decrease the translation efficiency of OSF-4. Therefore, a clone which contained the OSF-4-coding region alone was selected from the delation mutants prepared in Example 3, and it was used for the preparation of the expression vector for OSF-4. The segment of the clone from G of the 191st to A of the 2700th in SEQ ID NO: 1 in Sequence Listing was cut and a linker containing XhoI and BamHl sites and a linker containing XhoI site were ligated to the 5'-terminus and 3'-terminus of the segment, respectively. Then the segment bordered with XhoI site was inserted into the XhoI site of an expression plasmid vector for animal cells, pCXN2 (Niwa et al., (1991) Gene, vol.108, p193–200). The OSF-4 expression vector obtained was termed pMSS60 (FIG. 4).

The pMSS60 was introduced into L-cells of a fibroblast cell line derived from mouse epidermis by the calcium-phosphoric acid co-precipitating method. Then 12 G418 resistant colonies transformed by pMSS60 were cultured separately to obtain the cloned cell lines. RNA was extracted from these cloned cells. Then, three OSF-4-high producer cloned cell lines were selected with an RNA dot blotting method by using mouse OSF-4 cDNA as the probe. The three clones were termed C1,C7 and C11, respectively.

A band of approximately 100 kDa reacting with anti-OSF-4 antibody was detected by Western blotting analysis out of the proteins produced in these cloned cells.

Furthermore, the functional analysis of OSF-4 produced by these cloned cell lines was conducted as follows by Takeuchi's aggregation assay method which had been originally established to examine cadherin cell adhesive properties (Takeichi et al., (1977) J. Cell Biol., vol. 75, p464–474).

First, from each monolayer cells (C1, C7 and C11), TC-and TE-treated cell suspensions were prepared.

The TC-treated cell suspensions were prepared as follows. The monolayer cells were rinsed three times with CMF solution (Puck's $Ca^{2+}$ and $Mg^{2+}$ free saline; J. Exp. Med. vol.108, p954–956, 1958) containing 1 mM calcium chloride. Then, the cell suspensions were incubated at 37° C. for 15 min with HCMF solution (HEPES-buffered saline; 8.0 g of NaCl, 0.4 g of KCl, 0.09 g of $Na_2HPO_4$. $7H_2O$, 1 g of glucose, 2.38 g of HEPES, and 4.8 ml of 1N NaOH in 1,000 ml of $H_2O$, pH7.4) containing 0.01% trypsin and 0.1 mM calcium chloride.

The TE-treated cell suspensions were prepared by the same procedure as for preparation of TC-treated cell suspensions except incubation at 37° C. for 15 min with HCMF solution containing 1 mM EDTA and 0.01% trypsin.

Then, each cell suspension was rinsed with CMF solution twice and divided into cell suspensions containing $1 \times 10^6$ cells/3 ml in HCMF solution with or without 1 mM calcium chloride. Each cell suspension was transferred to a 15 ml-size conical tube and was allowed to make cell aggregation by stirring with 80 rpm at 37° C. for one hour. The ratio of N1/NO was calculated by counting with a Coulter-counter the number of cells before stirring (NO) and the number of cell clots after stirring (N1). The results are shown in Table 2; the OSF-4-expressing cloned cell lines showed calcim-dependent cell adhesive propertiy similar to cadherin. Cadherin molecule is known not to be digested by trypsin with calcium. Thus, the cell suspension treated with EDTA (TE-treated) were digested by trypsin and did not show any cell adhesion.

TABLE 5

Aggregation Assay of the cloned cell lines expressing mouse OSF-4

| Cell lines | No. of cell clots after 1 hr (N1)/ No. of cells pre-stirring (N0) | |
|---|---|---|
| | with 1 mM $Ca^{2+}$ | without 1 mM $Ca^{2+}$ |
| TC-treated | | |
| L-cell (Control) | 1.00(*1) | 1.00 |
| C1 | 0.65 | 1.00 |
| C7 | 0.29 | 1.00 |
| C11 | 0.51 | 1.00 |
| mock(*2) | 1.00 | 1.00 |
| TE-treated | | |
| C7 | 1.00 | 1.00 |

(*1)The smaller the number of cell clots after one-hour stirring, the stronger cell aggregation occured. The number 1.00 means no aggregation.
(*2)"Mock" refers to the control cell into which the vector alone was introduced.

OSF-4 provided by the present invention can be used as an agent for treating bone metabolic diseases, and its high organ specificity for bones enables its use as a diagnostic reagent for bone metabolic diseases.

TABLE 1

| | 1 | | | | 50 |
|---|---|---|---|---|---|
| mOSF-4 (SEQ ID NO:4) | MKENYCLQAA | LVCLSMLYHS | QAFALERRSH | LHPSFHGHHE | KGKEGQVLQR |
| hOSF-4-1 (SEQ ID NO:6) | MKENYCLQAA | LVCLGMLCHS | HAFAPERRGH | LRPSFHGHHE | KGKEGQVLQR |
| hOSF-4-2 (SEQ ID NO:12) | MKENYCLQAA | LVCLGMLCHS | HAFAPERRGH | LRPSFHGHHE | KGKEGQVLQR |
| Consensus (SEQ ID NO:12) | MKENYCLQAA | LVCL- ML- HS | - AFA- ERR- H | L- PSFHGHHE | KGKEGQVLQR |
| | | | | | 100 |
| mOSF-4 (SEQ ID NO:4) | SKRGWVWNQF | FVIEEYTGPD | PVLVGRLHSD | IDSGDGNIKY | ILSGEGAGTI |
| hOSF-4-1 (SEQ ID NO:6) | SKRGWVWNQF | FVIEEYTGPD | PVLVGRLHSD | IDSGDGNIKY | ILSGEGAGTI |
| hOSF-4-2 (SEQ ID NO:12) | SKRGWVWNQF | FVIEEYTGPD | PVLVGRLHSD | IDSGDGNIKY | ILSGEGAGTI |
| Consensus | SKRGWVWNQF | FVIEEYTGPD | PVLVGRLHSD | IDSGDGNIKY | ILSGEGAGTI |
| | 101 | | | | 150 |
| mOSF-4 (SEQ ID NO:4) | FVIDDKSGNI | HATKTLDREE | RAQYTLMAQA | VDRDTNRPLE | PPSEFIVKVQ |
| hOSF-4-1 (SEQ ID NO:6) | FVIDDKSGNI | HATKTLDREE | RAQYTLMAQA | VDRDTNRPLE | PPSEFIVKVQ |

TABLE 1-continued

| | | | | | |
|---|---|---|---|---|---|
| hOSF-4-2 (SEQ ID NO:12) | FVIDDKSGNI | HATKTLDREE | RAQYTLMAQA | VDRDTNRPLE | PPSEFIVKVQ |
| Consensus | FVIDDKSGNI | HATKTLDREE | RAQYTLMAQA | VDRDTNRPLE | PPSEFIVKVQ 200 |
| mOSF-4 (SEQ ID NO:4) | DINDNPPEFL | HEIYHANVPE | RSNVGTSVIQ | VTASDADDPT | YGNSAKLVYS |
| hOSF-4-1 (SEQ ID NO:6) | DINDNPPEFL | HETYHANVPE | RSNVGTSVIQ | VTASDADDPT | YGNSAKLVYS |
| hOSF-4-2 (SEQ ID NO:12) | DINDNPPEFL | HETYHANVPE | RSNVGTSVIQ | VTASDADDPT | YGNSAKLVYS |
| Consensus | DINDNPPEFL 201 | HE-YHANVPE | RSNVGTSVIQ | VTASDADDPT | YGNSAKLVYS 250 |
| mOSF-4 (SEQ ID NO:4) | ILEGQPYFSV | EAQTGIIRTA | LPNNDREAKE | EYHVVIQAKD | NGGHNGGLSG |
| hOSF-4-1 (SEQ ID NO:6) | ILEGQPYFSV | EAQTGIIRTA | LPNMDREAKE | EYHVVIQAKD | NGGHNGGLSG |
| hOSF-4-2 (SEQ ID NO:12) | ILEGQPYFSV | EAQTGIIRTA | LPNNDREAKE | EYHVVIQAKD | NGGHNGGLSG |
| Consensus | ILEGQPYFSV | EAQTGIIRTA | LPNNDREAKE | EYHVVIQAKD | NGGHNGGLSG 300 |
| mOSF-4 (SEQ ID NO:4) | TTKVTITLTD | VNDNPPKFPQ | SVYQMSVSEA | AVPGEEVGRV | KAKDPDIGEN |
| hOSF-4-1 (SEQ ID NO:6) | TTKVTITLTD | VNDNPPKFPQ | SVYQISVSEA | AVPGEEVGRV | KAKDPDIGEN |
| hOSF-4-2 (SEQ ID NO:12) | TTKVTITLTD | VNDNPPKFPQ | SVYQISVSEA | AVPGEEVGRV | KAKDPDIGEN |
| Consensus | TTKVTITLTD | VNDNPPKFPQ | SVYQ- SVSEA | AVPGEEVGRV | KAKDPDIGEN |

TABLE 2

| | | | | | |
|---|---|---|---|---|---|
| | 301 | | | | 350 |
| mOSF-4 | GLVTYNIVDG | DGIELFEITT | DYETQDGVVK | LKKPVDFETK | RAYSLKNEAA |
| hOSF-4-1 | GLVTYNIVDG | DGMESFEITT | DYETQEGVIK | LKKPVDFETK | RAYSLKVEAA |
| hOSF-4-2 | GLVTYNVDG | DGMESFEITT | DYETQEGVIK | LKKPVDFETK | RAYSLKVEAA |
| Consensus | GLVTYNIVDG | DG- E- FEITT | DYETQ- GV- K | LKKPVDFETK | RAYSLK- EAA 400 |
| mOSF-4 | NVHIDPKFIS | NGPFKDTVTV | KISVEDADEP | PMFLAPSYIH | EVQENAAAGT |
| hOSF-4-1 | NVHIDPKFIS | NGPFKDTVTV | KIAVEDADEP | PMFLAPSYIH | EVQENAAMGT |
| hOSF-4-2 | NVHIDPKFIS | NGPFKDTVTV | KIAVEDADEP | PMFLAPSYIH | EVQENAAMGT |
| Consensus | NVHIDPKFIS | NGPFKDTVTV | KI- VEDADEP | PMFLAPSYIH | EVQENAAAGT |
| | 401 | | | | 450 |
| mOSF-4 | VVGRVHAKDP | DAANSPIRYS | IDRHTDLDRF | FTINPEDGFI | KTTKPLDREE |
| hOSF-4-1 | VVGRVHAKDP | DAANSPNRYS | IDRHTDLDRF | FTINPEDGFI | KTTKPLDREE |
| hOSF-4-2 | VVGRVHAKDP | DAANSPNRYS | IDRHTDLDRF | FTINPEDGFI | KTTKPLDREE |
| Consensus | VVGRVHAKDP | DAANSPNRYS | IDRHTDLDRF | FTINPEDGFI | KTTKPLDREE 500 |
| mOSF-4 | TAWLNISVFA | AEIHNRHQET | KVPVAIRVLD | VNDNAPKFAA | PYEGFICESD |
| hOSF-4-1 | TAWLNITVFA | AEIHNRHQEA | KVPVAIRVLD | VHDNAPKFAA | PYEGFICESD |
| hOSF-4-2 | TAWLNITVFA | AEIHNRHQEA | KVPVAIRVLD | VNDNAPKFAA | PYEGFICESD |
| Consensus | TAWLHI- VFA | AEIHHRHQE- | KVPVAIRVLD | VNDHAPKFAA | PYEGFICESD |
| | 501 | | | | 550 |
| mOSF-4 | HPKALSNQPI | VTVSADDQDD | TANGPRFIFS | LPPEIMHNPN | FTVRDNRDNT |
| hOSF-4-1 | QTKPLSNQPI | VTISADDKDD | TANGPRFIFS | LPPEIIHHPN | FTVRDNRDNT |
| hOSF-4-2 | QTKPLSNQPI | VTISADDKDD | TANGPRFIFS | LPPEIIHNPN | FTVRDNRDNT |
| Consensus | - - K- LSNQPI | VT- SADD- DD | TANGPRFIFS | LPPEI- HNPN | FTVRDNRDNT 600 |
| mOSF-4 | AGVYARRGGF | SRQKQDFYLL | PIVISDGGIP | PMSSTNTLTI | KVCGCDVNGA |
| hOSF-4-1 | AGVYARRGGF | SRQKQDLYLL | PIVISDGGIP | PMSSTNTLTI | KVCGCDVNGA |
| hOSF-4-2 | AGVYARRGGF | SRQKQDLYLL | PIVISDGGIP | PMSSTNTLTI | KVCGCDVNGA |
| Consensus | AGVYARRGGF | SRQKQD- YLL | PIVISDGGIP | PMSSTNTLTI | KVCGCDVNGA |

TABLE 3

| | | | | | |
|---|---|---|---|---|---|
| | 601 | | | | 650 |
| mOSF-4 | LLSCNAEAYI | LNAGLSTGAL | IAILACIVIL | LVIVVLFVTL | RRQKKEPLIV |
| hOSF-4-1 | LLSCNAEAYI | LNAGLSTGAL | IAILACIVIL | LVIVVLFVTL | RRQKKEPLIV |
| hOSF-4-2 | LLSCNAEAYI | LNAGLSTGAL | IAILACIVIL | LGCPSLMEPP | SPREDMRLLY |
| Consensus | LLSCNAEAYI | LNAGLSTGAL | IAILACIVIL | L- - - - L- - - - | - - - - - - - L- - |
| | | | | | 700 |
| mOSF-4 | FEEEDVRENI | ITYDDEGGGE | EDTEAFDIAT | LQNPDGINGF | IPRKDIKPEY |
| hOSF-4-1 | FEEEDVRENI | ITYDDEGGGE | EDTEAFDIAT | LQNPDGINGF | IPRKDIKPEY |
| hOSF-4-2 | L- - - - - - - - - | - - - - - - - - - - | - - - - - - - - - - | - - - - - - - - - - | - - - - - - - - GF |
| Consensus | - - - - - - - - - - | - - - - - - - - - - | - - - - - - - - - - | - - - - - - - - - - | - - - - - - - - - - |
| | 701 | | | | 750 |

TABLE 3-continued

| | | | | | |
|---|---|---|---|---|---|
| mOSF-4 | QYMPRPGLRP | APNSVDVDDF | INTRIQEADN | DPTAPPYDSI | QIYGYEGRGS |
| hOSF-4-1 | QYMPRPGLRP | APNSVDVDDF | INTRIQEADN | DPTAPPYDSI | QIYGYEGRGS |
| hOSF-4-2 | QLMLFSYVKV | NRRFCLLGVF | IKLPFLYVVA | TESPTTLTSL | ---------- |
| Consensus | Q-M------- | ---------F | I--------- | --------S- | ---------- |
| | | | | | 796 |
| mOSF-4 | VAGSLSSLES | ATTDSDLDYD | YLQNWGPRFK | KLADLYGSKD | TFDDDS |
| hOSF-4-1 | VAGSLSSLES | ATTDSDLDYD | YLQNWGPRFK | KLADLYGSKD | TFDDDS |
| hOSF-4-2 | ---------- | ---------- | ---------- | ---------- | ------ |
| Consensus | ---------- | ---------- | ---------- | ---------- | ------ |

What is claimed is:

1. Isolated DNA coding for a polypeptide comprising a fragment of human OSF-4-2 having an amino acid sequence from amino acid 632 to 693 of SEQ ID NO:6, or human OSF-4-2 having an amino acid sequence at the 25th to 693rd positions in SEQ ID NO:6, said DNA being useful for detecting bone derived cells.

2. A process for the production of a recombinant mammalian OSF-4-2 protein encoded by DNA according to claim 1, comprising the steps of:

(a) obtaining a population of cells containing a heterogeneous DNA composed of the following DNA sequences:
    (i) a sequence which can function in the cells to control transcription and translation, and
    (ii) a DNA sequence joined downstream of said controlling sequence to code for said recombinant protein, and
  (b) culturing said population of cells under conditions which permit the production of said recombinant protein.

3. The process of claim 2, wherein the controlling sequence further contains a DNA coding for a signal peptide for secreting said recombinant protein extracellularly such that said DNA coding for said signal peptide is positioned immediately upstream of said DNA sequence coding for said recombinant protein comprising hOSF-4-2 having amino acids 25 to 693 of SEQ ID NO:6.

4. The process of claim 2, wherein the population of cells is *Escherichia coli,* or yeast, or mammalian cells.

5. The process of claim 3, wherein the population of cells is *Escherichia coli,* or yeast, or mammalian cells.

6. A diagnostic reagent for detecting bone derived cells, containing the DNA claim 1.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 3581 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Mus musculus
        ( B ) STRAIN: osteoblastic cell line MC3T3E1

( i x ) FEATURE:
        ( A ) NAME/KEY: CDS
        ( B ) LOCATION: 284..2671

( x i ) SEQUENCE DESCRIPTION: SEQ ID NO:1:

```
GAATTCGCGG  CCGCCTTTGA  AGACATTCAG  TTCTGTTATT  TATTGAATGA  CCAATCAGAT          60

GGGTGGAGCA  TGTTATAGGA  ATTGGCAGCA  GGTATCCAAT  GGGTGAAGAA  GAAGCTGACT         120

GCGGAGGTGA  CCAACCCTGG  CGTGATGTCC  TCAGTGAGTG  AAGATATTCC  ATTCCAGAGG         180

AGGTCTACTT  GACACATCTG  GGAGGCCGCC  ATCCGAAAGA  AAGCCACTCT  GTTGGTGTAG         240

GGAGTGACAG  CTGCATTCTC  CTGTGCCTAC  TGCATAACCA  AAA ATG AAG GAG AAC           295
                                                   Met Lys Glu Asn
                                                    1

TAC TGT TTA CAA GCT GCC CTG GTG TGC CTG AGC ATG CTA TAC CAC AGC              343
Tyr Cys Leu Gln Ala Ala Leu Val Cys Leu Ser Met Leu Tyr His Ser
 5              10                  15                  20

CAG GCG TTT GCT CTG GAG CGA CGA AGC CAC CTG CAT CCC TCT TTC CAT              391
Gln Ala Phe Ala Leu Glu Arg Arg Ser His Leu His Pro Ser Phe His
                25                  30                  35

GGA CAC CAT GAG AAG GGC AAG GAG GGG CAG GTG CTG CAA CGC TCC AAG              439
Gly His His Glu Lys Gly Lys Glu Gly Gln Val Leu Gln Arg Ser Lys
            40                  45                  50

AGA GGC TGG GTC TGG AAC CAA TTC TTT GTG ATA GAA GAG TAC ACC GGG              487
Arg Gly Trp Val Trp Asn Gln Phe Phe Val Ile Glu Glu Tyr Thr Gly
        55                  60                  65

CCT GAC CCT GTG CTG GTG GGC AGG CTT CAT TCT GAC ATT GAC TCC GGT              535
Pro Asp Pro Val Leu Val Gly Arg Leu His Ser Asp Ile Asp Ser Gly
    70                  75                  80

GAT GGG AAC ATT AAA TAC ATT CTC TCA GGT GAA GGA GCG GGA ACC ATT              583
Asp Gly Asn Ile Lys Tyr Ile Leu Ser Gly Glu Gly Ala Gly Thr Ile
85                  90                  95                 100

TTT GTG ATT GAT GAC AAA TCA GGG AAC ATT CAT GCC ACC AAG ACA TTG              631
```

-continued

|  |  |  |  |  |  |  |  |  |  |  |  |  |  |  |
|---|---|---|---|---|---|---|---|---|---|---|---|---|---|---|
| Phe | Val | Ile | Asp | Asp<br>105 | Lys | Ser | Gly | Asn | Ile<br>110 | His | Ala | Thr | Lys | Thr<br>115 | Leu |

| GAC | CGA | GAG | GAG | AGA | GCC | CAG | TAC | ACA | CTG | ATG | GCT | CAG | GCG | GTG | GAC | 679 |
| Asp | Arg | Glu | Glu<br>120 | Arg | Ala | Gln | Tyr | Thr<br>125 | Leu | Met | Ala | Gln | Ala<br>130 | Val | Asp |

| AGG | GAC | ACC | AAC | AGA | CCA | CTG | GAG | CCA | CCT | TCA | GAA | TTC | ATT | GTT | AAG | 727 |
| Arg | Asp | Thr<br>135 | Asn | Arg | Pro | Leu | Glu<br>140 | Pro | Pro | Ser | Glu | Phe<br>145 | Ile | Val | Lys |

| GTC | CAG | GAC | ATT | AAT | GAC | AAC | CCT | CCA | GAG | TTT | CTG | CAT | GAA | ATC | TAT | 775 |
| Val | Gln | Asp<br>150 | Ile | Asn | Asp | Asn<br>155 | Pro | Pro | Glu | Phe | Leu<br>160 | His | Glu | Ile | Tyr |

| CAT | GCC | AAT | GTG | CCT | GAG | AGG | TCC | AAT | GTG | GGA | ACA | TCA | GTT | ATC | CAA | 823 |
| His<br>165 | Ala | Asn | Val | Pro | Glu<br>170 | Arg | Ser | Asn | Val | Gly<br>175 | Thr | Ser | Val | Ile | Gln<br>180 |

| GTG | ACA | GCC | TCT | GAT | GCA | GAT | GAT | CCC | ACC | TAT | GGA | AAT | AGT | GCC | AAG | 871 |
| Val | Thr | Ala | Ser | Asp<br>185 | Ala | Asp | Asp | Pro | Thr<br>190 | Tyr | Gly | Asn | Ser | Ala<br>195 | Lys |

| TTA | GTG | TAT | AGC | ATC | CTT | GAA | GGA | CAA | CCC | TAT | TTC | TCG | GTG | GAG | GCC | 919 |
| Leu | Val | Tyr | Ser<br>200 | Ile | Leu | Glu | Gly | Gln<br>205 | Pro | Tyr | Phe | Ser | Val<br>210 | Glu | Ala |

| CAA | ACA | GGT | ATC | ATC | AGG | ACA | GCC | CTT | CCC | AAT | ATG | GAC | AGA | GAA | GCC | 967 |
| Gln | Thr | Gly<br>215 | Ile | Ile | Arg | Thr | Ala<br>220 | Leu | Pro | Asn | Met | Asp<br>225 | Arg | Glu | Ala |

| AAG | GAG | GAG | TAC | CAC | GTG | GTG | ATC | CAG | GCC | AAG | GAC | ATG | GGT | GGA | CAC | 1015 |
| Lys | Glu<br>230 | Glu | Tyr | His | Val | Val<br>235 | Ile | Gln | Ala | Lys | Asp<br>240 | Met | Gly | Gly | His |

| ATG | GGT | GGA | CTC | TCA | GGG | ACA | ACC | AAA | GTG | ACG | ATC | ACT | CTG | ACT | GAT | 1063 |
| Met | Gly<br>245 | Gly | Leu | Ser | Gly | Thr<br>250 | Thr | Lys | Val | Thr | Ile<br>255 | Thr | Leu | Thr | Asp<br>260 |

| GTC | AAC | GAC | AAC | CCA | CCA | AAG | TTT | CCA | CAG | AGC | GTG | TAC | CAG | ATG | TCT | 1111 |
| Val | Asn | Asp | Asn | Pro<br>265 | Pro | Lys | Phe | Pro | Gln<br>270 | Ser | Val | Tyr | Gln | Met<br>275 | Ser |

| GTA | TCA | GAA | GCA | GCT | GTC | CCG | GGG | GAG | GAA | GTA | GGA | AGG | GTG | AAG | GCT | 1159 |
| Val | Ser | Glu | Ala<br>280 | Ala | Val | Pro | Gly | Glu<br>285 | Glu | Val | Gly | Arg | Val<br>290 | Lys | Ala |

| AAA | GAC | CCA | GAC | ATT | GGA | GAA | AAT | GGC | TTA | GTC | ACA | TAC | AAT | ATC | GTT | 1207 |
| Lys | Asp | Pro | Asp<br>295 | Ile | Gly | Glu | Asn | Gly<br>300 | Leu | Val | Thr | Tyr | Asn<br>305 | Ile | Val |

| GAT | GGA | GAC | GGC | ATA | GAA | CTG | TTT | GAA | ATT | ACA | ACA | GAC | TAT | GAA | ACA | 1255 |
| Asp | Gly | Asp<br>310 | Gly | Ile | Glu | Leu | Phe<br>315 | Glu | Ile | Thr | Thr | Asp<br>320 | Tyr | Glu | Thr |

| CAG | GAT | GGT | GTG | GTG | AAG | CTG | AAA | AAG | CCT | GTA | GAT | TTT | GAA | ACC | AAA | 1303 |
| Gln | Asp<br>325 | Gly | Val | Val | Lys<br>330 | Leu | Lys | Lys | Pro | Val<br>335 | Asp | Phe | Glu | Thr | Lys<br>340 |

| AGA | GCT | TAT | AGC | TTG | AAG | ATA | GAG | GCC | GCC | AAT | GTT | CAC | ATT | GAT | CCG | 1351 |
| Arg | Ala | Tyr | Ser | Leu<br>345 | Lys | Ile | Glu | Ala | Ala<br>350 | Asn | Val | His | Ile | Asp<br>355 | Pro |

| AAG | TTC | ATC | AGC | AAT | GGA | CCT | TTC | AAG | GAC | ACT | GTG | ACC | GTC | AAG | ATT | 1399 |
| Lys | Phe | Ile | Ser<br>360 | Asn | Gly | Pro | Phe | Lys<br>365 | Asp | Thr | Val | Thr | Val<br>370 | Lys | Ile |

| TCA | GTA | GAA | GAT | GCC | GAT | GAG | CCT | CCC | ATG | TTC | TTG | GCC | CCA | AGT | TAT | 1447 |
| Ser | Val | Glu | Asp | Ala<br>375 | Asp | Glu | Pro | Pro | Met<br>380 | Phe | Leu | Ala | Pro | Ser<br>385 | Tyr |

| ATC | CAT | GAA | GTT | CAA | GAA | AAT | GCA | GCT | GCT | GGC | ACT | GTG | GTT | GGG | AGA | 1495 |
| Ile | His | Glu<br>390 | Val | Gln | Glu | Asn | Ala<br>395 | Ala | Ala | Gly | Thr | Val<br>400 | Val | Gly | Arg |

| GTA | CAT | GCC | AAA | GAC | CCA | GAT | GCT | GCC | AAC | AGC | CCA | ATA | AGG | TAT | TCA | 1543 |
| Val | His<br>405 | Ala | Lys | Asp | Pro | Asp<br>410 | Ala | Ala | Asn | Ser | Pro<br>415 | Ile | Arg | Tyr | Ser<br>420 |

| ATT | GAT | CGT | CAT | ACT | GAC | CTC | GAC | AGG | TTT | TTC | ACG | ATT | AAT | CCA | GAA | 1591 |

|  |  |  |  |  |  |  |  |  |  |  |  |  |  |  |  |  |
|---|---|---|---|---|---|---|---|---|---|---|---|---|---|---|---|---|
| Ile | Asp | Arg | His | Thr 425 | Asp | Leu | Asp | Arg 430 | Phe | Phe | Thr | Ile | Asn 435 | Pro | Glu | |
| GAT Asp | GGT Gly | TTT Phe | ATT Ile 440 | AAA Lys | ACT Thr | ACG Thr | AAA Lys | CCT Pro 445 | CTA Leu | GAT Asp | AGG Arg | GAA Glu | GAA Glu 450 | ACT Thr | GCC Ala | 1639 |
| TGG Trp | CTC Leu | AAC Asn 455 | ATC Ile | TCT Ser | GTC Val | TTC Phe | GCA Ala | GCA Ala 460 | GAA Glu | ATT Ile | CAC His | AAC Asn | AGA Arg 465 | CAT His | CAG Gln | 1687 |
| GAA Glu | ACC Thr 470 | AAA Lys | GTC Val | CCA Pro | GTG Val | GCC Ala | ATC Ile 475 | AGG Arg | GTC Val | CTG Leu | GAT Asp | GTC Val 480 | AAT Asn | GAC Asp | AAT Asn | 1735 |
| GCT Ala 485 | CCT Pro | AAG Lys | TTT Phe | GCT Ala | GCC Ala 490 | CCT Pro | TAT Tyr | GAA Glu | GGT Gly | TTT Phe 495 | ATC Ile | TGT Cys | GAG Glu | AGC Ser | GAT Asp 500 | 1783 |
| CAC His | CCC Pro | AAG Lys | GCA Ala | CTC Leu 505 | TCC Ser | AAC Asn | CAG Gln | CCA Pro | ATA Ile 510 | GTT Val | ACA Thr | GTT Val | AGT Ser | GCA Ala 515 | GAT Asp | 1831 |
| GAC Asp | CAG Gln | GAC Asp | GAC Asp 520 | ACA Thr | GCC Ala | AAT Asn | GGA Gly | CCA Pro 525 | AGA Arg | TTT Phe | ATC Ile | TTC Phe | AGC Ser 530 | CTA Leu | CCC Pro | 1879 |
| CCT Pro | GAA Glu | ATC Ile 535 | ATG Met | CAC His | AAC Asn | CCA Pro | AAC Asn 540 | TTC Phe | ACA Thr | GTA Val | AGA Arg | GAC Asp 545 | AAC Asn | AGA Arg | GAT Asp | 1927 |
| AAC Asn | ACT Thr 550 | GCA Ala | GGA Gly | GTA Val | TAT Tyr | GCC Ala 555 | CGA Arg | CGT Arg | GGA Gly | GGG Gly | TTC Phe 560 | AGT Ser | CGG Arg | CAG Gln | AAG Lys | 1975 |
| CAG Gln 565 | GAC Asp | TTC Phe | TAC Tyr | CTC Leu | CTG Leu 570 | CCC Pro | ATT Ile | GTG Val | ATC Ile | AGT Ser 575 | GAT Asp | GGT Gly | GGC Gly | ATT Ile | CCA Pro 580 | 2023 |
| CCT Pro | ATG Met | AGT Ser | AGC Ser | ACC Thr 585 | AAT Asn | ACC Thr | CTC Leu | ACT Thr | ATC Ile 590 | AAA Lys | GTC Val | TGT Cys | GGC Gly | TGT Cys | GAT Asp 595 | 2071 |
| GTG Val | AAT Asn | GGG Gly | GCA Ala 600 | CTG Leu | TTG Leu | TCC Ser | TGT Cys | AAC Asn 605 | GCT Ala | GAA Glu | GCC Ala | TAC Tyr | ATC Ile 610 | CTG Leu | AAT Asn | 2119 |
| GCC Ala | GGT Gly | CTG Leu 615 | AGC Ser | ACT Thr | GGG Gly | GCA Ala | CTG Leu 620 | ATC Ile | GCC Ala | ATC Ile | CTT Leu | GCC Ala 625 | TGC Cys | ATC Ile | GTC Val | 2167 |
| ATT Ile | CTT Leu 630 | CTG Leu | GTC Val | ATC Ile | GTT Val | GTG Val 635 | CTG Leu | TTT Phe | GTT Val | ACC Thr | CTG Leu 640 | AGG Arg | AGG Arg | CAA Gln | AAG Lys | 2215 |
| AAA Lys 645 | GAA Glu | CCA Pro | CTC Leu | ATT Ile | GTA Val 650 | TTT Phe | GAA Glu | GAG Glu | GAG Glu | GAT Asp 655 | GTC Val | CGT Arg | GAG Glu | AAC Asn | ATC Ile 660 | 2263 |
| ATA Ile | ACC Thr | TAT Tyr | GAT Asp | GAT Asp 665 | GAA Glu | GGG Gly | GGT Gly | GGT Gly | GAG Glu 670 | GAA Glu | GAC Asp | ACT Thr | GAA Glu | GCC Ala 675 | TTC Phe | 2311 |
| GAC Asp | ATA Ile | GCC Ala | ACC Thr 680 | CTG Leu | CAG Gln | AAT Asn | CCT Pro | GAC Asp 685 | GGC Gly | ATC Ile | AAT Asn | GGA Gly | TTT Phe 690 | ATC Ile | CCT Pro | 2359 |
| CGC Arg | AAA Lys | GAT Asp 695 | ATC Ile | AAA Lys | CCT Pro | GAG Glu | TAT Tyr 700 | CAG Gln | TAT Tyr | ATG Met | CCT Pro | AGA Arg 705 | CCT Pro | GGG Gly | CTG Leu | 2407 |
| CGA Arg | CCA Pro 710 | GCA Ala | CCC Pro | AAC Asn | AGT Ser | GTG Val 715 | GAT Asp | GTG Val | GAC Asp | GAC Asp | TTC Phe 720 | ATC Ile | AAC Asn | ACA Thr | AGA Arg | 2455 |
| ATA Ile 725 | CAG Gln | GAG Glu | GCA Ala | GAT Asp | AAT Asn 730 | GAT Asp | CCC Pro | ACA Thr | GCC Ala | CCT Pro 735 | CCC Pro | TAT Tyr | GAC Asp | TCC Ser | ATC Ile 740 | 2503 |
| CAA Gln | ATC Ile | TAT Tyr | GGT Gly | TAT Tyr | GAG Glu | GGC Gly | CGG Arg | GGT Gly | TCC Ser | GTG Val | GCT Ala | GGG Gly | TCC Ser | CTG Leu | AGC Ser | 2551 |

|  |  |  |  |  |  |  |  |  |  |  |  |  |  |  |  |  |
|---|---|---|---|---|---|---|---|---|---|---|---|---|---|---|---|---|
| Gln | Ile | Tyr | Gly<br>745 | Tyr | Glu | Gly | Arg | Gly<br>750 | Ser | Val | Ala | Gly | Ser<br>755 | Leu | Ser | |

| TCC | TTG | GAG | TCT | GCC | ACG | ACA | GAC | TCA | GAC | CTG | GAC | TAC | GAC | TAT | CTA | 2599 |
|---|---|---|---|---|---|---|---|---|---|---|---|---|---|---|---|---|
| Ser | Leu | Glu | Ser<br>760 | Ala | Thr | Thr | Asp | Ser<br>765 | Asp | Leu | Asp | Tyr | Asp<br>770 | Tyr | Leu | |

| CAG | AAC | TGG | GGA | CCT | CGT | TTT | AAG | AAA | CTG | GCA | GAC | TTG | TAT | GGC | TCC | 2647 |
|---|---|---|---|---|---|---|---|---|---|---|---|---|---|---|---|---|
| Gln | Asn | Trp<br>775 | Gly | Pro | Arg | Phe | Lys<br>780 | Lys | Leu | Ala | Asp | Leu<br>785 | Tyr | Gly | Ser | |

| AAA | GAC | ACT | TTT | GAT | GAT | GAC | TCT | TAACAATAAT | GTTACAAATT | TGGCCTTAAG | 2701 |
|---|---|---|---|---|---|---|---|---|---|---|---|
| Lys | Asp<br>790 | Thr | Phe | Asp | Asp | Asp<br>795 | Ser | | | | |

| AACTGTGTCT | GGCATTCTCA | AGAATCTAGA | AGATGTGTAA | ACAGGTATTT | TTTTAAATCA | 2761 |
|---|---|---|---|---|---|---|
| AGGAAAGGCT | CATTTAAAAC | AAGCAGAGTT | TTACAGAGAG | GAAACATTTA | ATAAAACTGC | 2821 |
| AAGGACATCA | AAGTGGAAAA | TACTGTGAAG | TACCTTTTCC | CACTTAAAAA | GCAAATATTG | 2881 |
| AAGTTGTTTA | TCAACTTCAG | TAGAAAAAAA | AAAACCACTT | GGCACACAAA | ATATTTAAAT | 2941 |
| GAAGGAGAAG | TCCACGGTGA | ACTTACAATG | AAGGGAAATC | GTCTATGTGT | TAAGAACATC | 3001 |
| TAAGTCTCTC | TTATTTTATT | TTTTAATTTG | TCAAAGAAGC | TTCCACAAAA | TTAGAAAGGA | 3061 |
| CAACAGTTCT | GAGCTGAAAT | TTCGCCTTAA | ACTATGGACA | CTCTATCTGT | AGTGCGTTTT | 3121 |
| TAAACTTTGA | ATATATAATA | TCCAGCCAGC | TTAAACCCAT | ACAATGTATG | TACAATACAA | 3181 |
| TGTACAATTA | TGTCTCTTGA | GCATCAATCT | TGTTACTGCT | GATTCTTGTA | AATCTTTTG | 3241 |
| CTTCTACTTT | CATCCTAAAC | TAATACGTGC | CAGATATAAC | TGTCTTGTTT | CAGTGAGGAG | 3301 |
| CACCCTATTT | CTATGTCATT | TTTAATGTAT | CTATTTGTAC | AATTTTAAAG | TTCTTATTTT | 3361 |
| AGTATACATA | CAAATATCAG | TATTCTGACA | TGTACGAAAA | TGTTACAGCA | TCACACTTAT | 3421 |
| ATTTTATGAA | CATTGTACTG | TTGCTTTAAT | ATGAGCTTCA | ATATAAGAAG | CAACCTTTGA | 3481 |
| AATAAAAAAA | AGATTCTTTT | TTAAAAAAAA | AAAAAAAAAA | AAAAAAAAAA | AAAAAAAAAA | 3541 |
| AAAAAAAAAA | AAAAAAAAAA | AAAAAGCGG | CCGCGAATTC | | | 3581 |

(2) INFORMATION FOR SEQ ID NO:2:

(i) SEQUENCE CHARACTERISTICS:
        (A) LENGTH: 796 amino acids
        (B) TYPE: amino acid
        (D) TOPOLOGY: linear (ii) MOLECULE TYPE: protein (xi) SEQUENCE DESCRIPTION: SEQ ID NO:2:

| Met<br>1 | Lys | Glu | Asn | Tyr<br>5 | Cys | Leu | Gln | Ala | Ala<br>10 | Leu | Val | Cys | Leu | Ser<br>15 | Met |
|---|---|---|---|---|---|---|---|---|---|---|---|---|---|---|---|
| Leu | Tyr | His | Ser<br>20 | Gln | Ala | Phe | Ala | Leu<br>25 | Glu | Arg | Arg | Ser | His<br>30 | Leu | His |
| Pro | Ser | Phe<br>35 | His | Gly | His | His | Glu<br>40 | Lys | Gly | Lys | Glu | Gly<br>45 | Gln | Val | Leu |
| Gln | Arg<br>50 | Ser | Lys | Arg | Gly | Trp<br>55 | Val | Trp | Asn | Gln | Phe<br>60 | Phe | Val | Ile | Glu |
| Glu<br>65 | Tyr | Thr | Gly | Pro | Asp<br>70 | Pro | Val | Leu | Val | Gly<br>75 | Arg | Leu | His | Ser | Asp<br>80 |
| Ile | Asp | Ser | Gly | Asp<br>85 | Gly | Asn | Ile | Lys | Tyr<br>90 | Ile | Leu | Ser | Gly | Glu<br>95 | Gly |
| Ala | Gly | Thr | Ile<br>100 | Phe | Val | Ile | Asp | Asp<br>105 | Lys | Ser | Gly | Asn | Ile<br>110 | His | Ala |
| Thr | Lys | Thr<br>115 | Leu | Asp | Arg | Glu | Glu<br>120 | Arg | Ala | Gln | Tyr | Thr<br>125 | Leu | Met | Ala |

```
Gln Ala Val Asp Arg Asp Thr Asn Arg Pro Leu Glu Pro Pro Ser Glu
    130                 135                 140
Phe Ile Val Lys Val Gln Asp Ile Asn Asp Asn Pro Pro Glu Phe Leu
145             150                 155                     160
His Glu Ile Tyr His Ala Asn Val Pro Glu Arg Ser Asn Val Gly Thr
                165                 170                 175
Ser Val Ile Gln Val Thr Ala Ser Asp Ala Asp Pro Thr Tyr Gly
            180                 185                 190
Asn Ser Ala Lys Leu Val Tyr Ser Ile Leu Glu Gly Gln Pro Tyr Phe
        195                 200                 205
Ser Val Glu Ala Gln Thr Gly Ile Ile Arg Thr Ala Leu Pro Asn Met
    210                 215                 220
Asp Arg Glu Ala Lys Glu Glu Tyr His Val Val Ile Gln Ala Lys Asp
225                 230                 235                 240
Met Gly Gly His Met Gly Gly Leu Ser Gly Thr Thr Lys Val Thr Ile
                245                 250                 255
Thr Leu Thr Asp Val Asn Asp Asn Pro Pro Lys Phe Pro Gln Ser Val
            260                 265                 270
Tyr Gln Met Ser Val Ser Glu Ala Ala Val Pro Gly Glu Glu Val Gly
        275                 280                 285
Arg Val Lys Ala Lys Asp Pro Asp Ile Gly Glu Asn Gly Leu Val Thr
    290                 295                 300
Tyr Asn Ile Val Asp Gly Asp Gly Ile Glu Leu Phe Glu Ile Thr Thr
305                 310                 315                 320
Asp Tyr Glu Thr Gln Asp Gly Val Val Lys Leu Lys Lys Pro Val Asp
                325                 330                 335
Phe Glu Thr Lys Arg Ala Tyr Ser Leu Lys Ile Glu Ala Ala Asn Val
            340                 345                 350
His Ile Asp Pro Lys Phe Ile Ser Asn Gly Pro Phe Lys Asp Thr Val
        355                 360                 365
Thr Val Lys Ile Ser Val Glu Asp Ala Asp Glu Pro Pro Met Phe Leu
    370                 375                 380
Ala Pro Ser Tyr Ile His Glu Val Gln Glu Asn Ala Ala Ala Gly Thr
385                 390                 395                 400
Val Val Gly Arg Val His Ala Lys Asp Pro Asp Ala Ala Asn Ser Pro
                405                 410                 415
Ile Arg Tyr Ser Ile Asp Arg His Thr Asp Leu Asp Arg Phe Phe Thr
            420                 425                 430
Ile Asn Pro Glu Asp Gly Phe Ile Lys Thr Thr Lys Pro Leu Asp Arg
        435                 440                 445
Glu Glu Thr Ala Trp Leu Asn Ile Ser Val Phe Ala Ala Glu Ile His
    450                 455                 460
Asn Arg His Gln Glu Thr Lys Val Pro Val Ala Ile Arg Val Leu Asp
465                 470                 475                 480
Val Asn Asp Asn Ala Pro Lys Phe Ala Ala Pro Tyr Glu Gly Phe Ile
                485                 490                 495
Cys Glu Ser Asp His Pro Lys Ala Leu Ser Asn Gln Pro Ile Val Thr
            500                 505                 510
Val Ser Ala Asp Asp Gln Asp Thr Ala Asn Gly Pro Arg Phe Ile
        515                 520                 525
Phe Ser Leu Pro Pro Glu Ile Met His Asn Pro Asn Phe Thr Val Arg
    530                 535                 540
Asp Asn Arg Asp Asn Thr Ala Gly Val Tyr Ala Arg Arg Gly Gly Phe
```

|     |     |     |     | 545 |     |     |     |     | 550 |     |     |     |     | 555 |     |     |     |     | 560 |
| --- | --- | --- | --- | --- | --- | --- | --- | --- | --- | --- | --- | --- | --- | --- | --- | --- | --- | --- | --- |
| Ser | Arg | Gln | Lys | Gln | Asp | Phe | Tyr | Leu | Leu | Pro | Ile | Val | Ile | Ser | Asp |
|     |     |     |     | 565 |     |     |     |     | 570 |     |     |     |     | 575 |     |
| Gly | Gly | Ile | Pro | Pro | Met | Ser | Ser | Thr | Asn | Thr | Leu | Thr | Ile | Lys | Val |
|     |     |     | 580 |     |     |     |     | 585 |     |     |     |     | 590 |     |     |
| Cys | Gly | Cys | Asp | Val | Asn | Gly | Ala | Leu | Leu | Ser | Cys | Asn | Ala | Glu | Ala |
|     |     | 595 |     |     |     |     | 600 |     |     |     |     | 605 |     |     |     |
| Tyr | Ile | Leu | Asn | Ala | Gly | Leu | Ser | Thr | Gly | Ala | Leu | Ile | Ala | Ile | Leu |
| 610 |     |     |     |     | 615 |     |     |     |     | 620 |     |     |     |     |     |
| Ala | Cys | Ile | Val | Ile | Leu | Leu | Val | Ile | Val | Val | Leu | Phe | Val | Thr | Leu |
| 625 |     |     |     |     | 630 |     |     |     |     | 635 |     |     |     |     | 640 |
| Arg | Arg | Gln | Lys | Lys | Glu | Pro | Leu | Ile | Val | Phe | Glu | Glu | Glu | Asp | Val |
|     |     |     |     | 645 |     |     |     |     | 650 |     |     |     |     | 655 |     |
| Arg | Glu | Asn | Ile | Ile | Thr | Tyr | Asp | Asp | Glu | Gly | Gly | Gly | Glu | Glu | Asp |
|     |     |     | 660 |     |     |     |     | 665 |     |     |     |     | 670 |     |     |
| Thr | Glu | Ala | Phe | Asp | Ile | Ala | Thr | Leu | Gln | Asn | Pro | Asp | Gly | Ile | Asn |
|     |     | 675 |     |     |     |     | 680 |     |     |     |     | 685 |     |     |     |
| Gly | Phe | Ile | Pro | Arg | Lys | Asp | Ile | Lys | Pro | Glu | Tyr | Gln | Tyr | Met | Pro |
|     | 690 |     |     |     |     | 695 |     |     |     |     | 700 |     |     |     |     |
| Arg | Pro | Gly | Leu | Arg | Pro | Ala | Pro | Asn | Ser | Val | Asp | Val | Asp | Asp | Phe |
| 705 |     |     |     | 710 |     |     |     |     | 715 |     |     |     |     | 720 |     |
| Ile | Asn | Thr | Arg | Ile | Gln | Glu | Ala | Asp | Asn | Asp | Pro | Thr | Ala | Pro | Pro |
|     |     |     | 725 |     |     |     |     | 730 |     |     |     |     | 735 |     |     |
| Tyr | Asp | Ser | Ile | Gln | Ile | Tyr | Gly | Tyr | Glu | Gly | Arg | Gly | Ser | Val | Ala |
|     |     |     | 740 |     |     |     |     | 745 |     |     |     |     | 750 |     |     |
| Gly | Ser | Leu | Ser | Ser | Leu | Glu | Ser | Ala | Thr | Thr | Asp | Ser | Asp | Leu | Asp |
|     |     | 755 |     |     |     |     | 760 |     |     |     |     | 765 |     |     |     |
| Tyr | Asp | Tyr | Leu | Gln | Asn | Trp | Gly | Pro | Arg | Phe | Lys | Lys | Leu | Ala | Asp |
|     | 770 |     |     |     |     | 775 |     |     |     |     | 780 |     |     |     |     |
| Leu | Tyr | Gly | Ser | Lys | Asp | Thr | Phe | Asp | Asp | Asp | Ser |     |     |     |     |
| 785 |     |     |     |     | 790 |     |     |     |     | 795 |     |     |     |     |     |

( 2 ) INFORMATION FOR SEQ ID NO:3:

( i ) SEQUENCE CHARACTERISTICS:
        ( A ) LENGTH: 3712 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Homo sapiens
        ( F ) TISSUE TYPE: Osteosarcoma ( i x ) FEATURE:
        ( A ) NAME/KEY: CDS
        ( B ) LOCATION: 461..2848

( x i ) SEQUENCE DESCRIPTION: SEQ ID NO:3:

| | | | | | |
| --- | --- | --- | --- | --- | --- |
| GAATTCGGAG | ATCTACAGGC | GAGGAGAGAT | GCCGCGGGGG | CCGCTCGCAG | CCGCCGCTGA | 60 |
| CTTGTGAATG | GGACCGGGAC | TGGGGCCGGG | ACTGACACCG | CAGCGCTTGC | CCTGCGCCAG | 120 |
| GGACTGGCGG | CTCGGAGGTT | GCGTCCACCC | TCAAGGGCCC | CAGAAATCAC | TGTGTTTTCA | 180 |
| GCTCAGCGGC | CCTGTGACAT | TCCTTCGTGT | TGTCATTTGT | TGAGTGACCA | ATCAGATGGG | 240 |
| TGGAGTGTGT | TACAGAAATT | GGCAGCAAGT | ATCCAATGGG | TGAAGAAGAA | GCTAACTGGG | 300 |
| GACGTGGGCA | GCCCTGACGT | GATGAGCTCA | ACCAGCAGAG | ACATTCCATC | CCAAGAGAGG | 360 |

-continued

```
TCTGCGTGAC GCGTCCGGGA GGCCACCCTC AGCAAGACCA CCGTACAGTT GGTGGAAGGG         420

GTGACAGCTG CATTCTCCTG TGCCTACCAC GTAACCAAAA ATG AAG GAG AAC TAC           475
                                              Met Lys Glu Asn Tyr
                                              1               5

TGT TTA CAA GCC GCC CTG GTG TGC CTG GGC ATG CTG TGC CAC AGC CAT           523
Cys Leu Gln Ala Ala Leu Val Cys Leu Gly Met Leu Cys His Ser His
                10              15                  20

GCC TTT GCC CCA GAG CGG CGG GGG CAC CTG CGG CCC TCC TTC CAT GGG           571
Ala Phe Ala Pro Glu Arg Arg Gly His Leu Arg Pro Ser Phe His Gly
            25              30              35

CAC CAT GAG AAG GGC AAG GAG GGG CAG GTG CTA CAG CGC TCC AAG CGT           619
His His Glu Lys Gly Lys Glu Gly Gln Val Leu Gln Arg Ser Lys Arg
        40              45              50

GGC TGG GTC TGG AAC CAG TTC TTC GTG ATA GAG GAG TAC ACC GGG CCT           667
Gly Trp Val Trp Asn Gln Phe Phe Val Ile Glu Glu Tyr Thr Gly Pro
    55              60              65

GAC CCC GTG CTT GTG GGC AGG CTT CAT TCA GAT ATT GAC TCT GGT GAT           715
Asp Pro Val Leu Val Gly Arg Leu His Ser Asp Ile Asp Ser Gly Asp
70              75              80                      85

GGG AAC ATT AAA TAC ATT CTC TCA GGG GAA GGA GCT GGA ACC ATT TTT           763
Gly Asn Ile Lys Tyr Ile Leu Ser Gly Glu Gly Ala Gly Thr Ile Phe
            90              95                  100

GTG ATT GAT GAC AAA TCA GGG AAC ATT CAT GCC ACC AAG ACG TTG GAT           811
Val Ile Asp Asp Lys Ser Gly Asn Ile His Ala Thr Lys Thr Leu Asp
            105             110             115

CGA GAA GAG AGA GCC CAG TAC ACG TTG ATG GCT CAG GCG GTG GAC AGG           859
Arg Glu Glu Arg Ala Gln Tyr Thr Leu Met Ala Gln Ala Val Asp Arg
        120             125             130

GAC ACC AAT CGG CCA CTG GAG CCA CCG TCG GAA TTC ATT GTC AAG GTC           907
Asp Thr Asn Arg Pro Leu Glu Pro Pro Ser Glu Phe Ile Val Lys Val
    135             140             145

CAG GAC ATT AAT GAC AAC CCT CCG GAG TTC CTG CAC GAG ACC TAT CAT           955
Gln Asp Ile Asn Asp Asn Pro Pro Glu Phe Leu His Glu Thr Tyr His
150             155             160                     165

GCC AAC GTG CCT GAG AGG TCC AAT GTG GGA ACG TCA GTA ATC CAG GTG          1003
Ala Asn Val Pro Glu Arg Ser Asn Val Gly Thr Ser Val Ile Gln Val
            170             175                     180

ACA GCT TCA GAT GCA GAT GAC CCC ACT TAT GGA AAT AGC GCC AAG TTA          1051
Thr Ala Ser Asp Ala Asp Asp Pro Thr Tyr Gly Asn Ser Ala Lys Leu
            185             190                 195

GTG TAC AGT ATC CTC GAA GGA CAA CCC TAT TTT TCG GTG GAA GCA CAG          1099
Val Tyr Ser Ile Leu Glu Gly Gln Pro Tyr Phe Ser Val Glu Ala Gln
        200             205                 210

ACA GGT ATC ATC AGA ACA GCC CTA CCC AAC ATG GAC AGG GAG GCC AAG          1147
Thr Gly Ile Ile Arg Thr Ala Leu Pro Asn Met Asp Arg Glu Ala Lys
    215             220             225

GAG GAG TAC CAC GTG GTG ATC CAG GCC AAG GAC ATG GGT GGA CAT ATG          1195
Glu Glu Tyr His Val Val Ile Gln Ala Lys Asp Met Gly Gly His Met
230             235             240                     245

GGC GGA CTC TCA GGG ACA ACC AAA GTG ACG ATC ACA CTG ACC GAT GTC          1243
Gly Gly Leu Ser Gly Thr Thr Lys Val Thr Ile Thr Leu Thr Asp Val
            250             255                     260

AAT GAC AAC CCA CCA AAG TTT CCG CAG AGC GTA TAC CAG ATA TCT GTG          1291
Asn Asp Asn Pro Pro Lys Phe Pro Gln Ser Val Tyr Gln Ile Ser Val
            265             270                 275

TCA GAA GCA GCC GTC CCT GGG GAG GAA GTA GGA AGA GTG AAA GCT AAA          1339
Ser Glu Ala Ala Val Pro Gly Glu Glu Val Gly Arg Val Lys Ala Lys
            280             285                 290

GAT CCA GAC ATT GGA GAA AAT GGC TTA GTC ACA TAC AAT ATT GTT GAT          1387
Asp Pro Asp Ile Gly Glu Asn Gly Leu Val Thr Tyr Asn Ile Val Asp
```

```
                              295                                    300                                    305
GGA  GAT  GGT  ATG  GAA  TCG  TTT  GAA  ATC  ACA  ACG  GAT  TAT  GAA  ACA  CAG       1435
Gly  Asp  Gly  Met  Glu  Ser  Phe  Glu  Ile  Thr  Thr  Asp  Tyr  Glu  Thr  Gln
310                      315                     320                          325

GAG  GGG  GTG  ATA  AAG  CTG  AAA  AAG  CCT  GTA  GAT  TTT  GAA  ACC  AAA  AGA       1483
Glu  Gly  Val  Ile  Lys  Leu  Lys  Lys  Pro  Val  Asp  Phe  Glu  Thr  Lys  Arg
                    330                     335                          340

GCC  TAT  AGC  TTG  AAG  GTA  GAG  GCA  GCC  AAC  GTG  CAC  ATC  GAC  CCG  AAG       1531
Ala  Tyr  Ser  Leu  Lys  Val  Glu  Ala  Ala  Asn  Val  His  Ile  Asp  Pro  Lys
               345                     350                     355

TTT  ATC  AGC  AAT  GGC  CCT  TTC  AAG  GAC  ACT  GTG  ACC  GTC  AAG  ATC  GCA       1579
Phe  Ile  Ser  Asn  Gly  Pro  Phe  Lys  Asp  Thr  Val  Thr  Val  Lys  Ile  Ala
          360                     365                     370

GTA  GAA  GAT  GCT  GAT  GAG  CCC  CCT  ATG  TTC  TTG  GCC  CCA  AGT  TAC  ATC       1627
Val  Glu  Asp  Ala  Asp  Glu  Pro  Pro  Met  Phe  Leu  Ala  Pro  Ser  Tyr  Ile
     375                     380                     385

CAC  GAA  GTC  CAA  GAA  AAT  GCA  GCT  GCT  GGC  ACC  GTG  GTT  GGG  AGA  GTG       1675
His  Glu  Val  Gln  Glu  Asn  Ala  Ala  Ala  Gly  Thr  Val  Val  Gly  Arg  Val
390                     395                     400                          405

CAT  GCC  AAA  GAC  CCT  GAT  GCT  GCC  AAC  AGC  CCG  ATA  AGG  TAT  TCC  ATC       1723
His  Ala  Lys  Asp  Pro  Asp  Ala  Ala  Asn  Ser  Pro  Ile  Arg  Tyr  Ser  Ile
                    410                     415                          420

GAT  CGT  CAC  ACT  GAC  CTC  GAC  AGA  TTT  TTC  ACT  ATT  AAT  CCA  GAG  GAT       1771
Asp  Arg  His  Thr  Asp  Leu  Asp  Arg  Phe  Phe  Thr  Ile  Asn  Pro  Glu  Asp
               425                     430                     435

GGT  TTT  ATT  AAA  ACT  ACA  AAA  CCT  CTG  GAT  AGA  GAG  GAA  ACA  GCC  TGG       1819
Gly  Phe  Ile  Lys  Thr  Thr  Lys  Pro  Leu  Asp  Arg  Glu  Glu  Thr  Ala  Trp
          440                     445                     450

CTC  AAC  ATC  ACT  GTC  TTT  GCA  GCA  GAA  ATC  CAC  AAT  CGG  CAT  CAG  GAA       1867
Leu  Asn  Ile  Thr  Val  Phe  Ala  Ala  Glu  Ile  His  Asn  Arg  His  Gln  Glu
     455                     460                     465

GCC  AAA  GTC  CCA  GTG  GCC  ATT  AGG  GTC  CTT  GAT  GTC  AAC  GAT  AAT  GCT       1915
Ala  Lys  Val  Pro  Val  Ala  Ile  Arg  Val  Leu  Asp  Val  Asn  Asp  Asn  Ala
470                     475                     480                          485

CCC  AAG  TTT  GCT  GCC  CCT  TAT  GAA  GGT  TTC  ATC  TGT  GAG  AGT  GAT  CAG       1963
Pro  Lys  Phe  Ala  Ala  Pro  Tyr  Glu  Gly  Phe  Ile  Cys  Glu  Ser  Asp  Gln
                    490                     495                          500

ACC  AAG  CCA  CTT  TCC  AAC  CAG  CCA  ATT  GTT  ACA  ATT  AGT  GCA  GAT  GAC       2011
Thr  Lys  Pro  Leu  Ser  Asn  Gln  Pro  Ile  Val  Thr  Ile  Ser  Ala  Asp  Asp
               505                     510                     515

AAG  GAT  GAC  ACG  GCC  AAT  GGA  CCA  AGA  TTT  ATC  TTC  AGC  CTA  CCC  CCT       2059
Lys  Asp  Asp  Thr  Ala  Asn  Gly  Pro  Arg  Phe  Ile  Phe  Ser  Leu  Pro  Pro
          520                     525                     530

GAA  ATC  ATT  CAC  AAT  CCA  AAT  TTC  ACA  GTC  AGA  GAC  AAC  CGA  GAT  AAC       2107
Glu  Ile  Ile  His  Asn  Pro  Asn  Phe  Thr  Val  Arg  Asp  Asn  Arg  Asp  Asn
     535                     540                     545

ACA  GCA  GGC  GTG  TAC  GCC  CGG  CGT  GGA  GGG  TTC  AGT  CGG  CAG  AAG  CAG       2155
Thr  Ala  Gly  Val  Tyr  Ala  Arg  Arg  Gly  Gly  Phe  Ser  Arg  Gln  Lys  Gln
550                     555                     560                          565

GAC  TTG  TAC  CTT  CTG  CCC  ATA  GTG  ATC  AGC  GAT  GGC  GGC  ATC  CCG  CCC       2203
Asp  Leu  Tyr  Leu  Leu  Pro  Ile  Val  Ile  Ser  Asp  Gly  Gly  Ile  Pro  Pro
                    570                     575                          580

ATG  AGT  AGC  ACC  AAC  ACC  CTC  ACC  ATC  AAA  GTC  TGC  GGG  TGC  GAC  GTG       2251
Met  Ser  Ser  Thr  Asn  Thr  Leu  Thr  Ile  Lys  Val  Cys  Gly  Cys  Asp  Val
               585                     590                     595

AAC  GGG  GCA  CTG  CTC  TCC  TGC  AAC  GCA  GAG  GCC  TAC  ATT  CTG  AAC  GCC       2299
Asn  Gly  Ala  Leu  Leu  Ser  Cys  Asn  Ala  Glu  Ala  Tyr  Ile  Leu  Asn  Ala
          600                     605                     610

GGC  CTG  AGC  ACA  GGC  GCC  CTG  ATC  GCC  ATC  CTC  GCC  TGC  ATC  GTC  ATT       2347
Gly  Leu  Ser  Thr  Gly  Ala  Leu  Ile  Ala  Ile  Leu  Ala  Cys  Ile  Val  Ile
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
|     |     | 615 |     |     |     |     | 620 |     |     |     |     | 625 |     |     |     |     |
| CTC | CTG | GTC | ATT | GTA | GTA | TTG | TTT | GTG | ACC | CTG | AGA | AGG | CAA | AAG | AAA | 2395 |
| Leu | Leu | Val | Ile | Val | Val | Leu | Phe | Val | Thr | Leu | Arg | Arg | Gln | Lys | Lys |     |
| 630 |     |     |     | 635 |     |     |     |     | 640 |     |     |     |     | 645 |     |     |
| GAA | CCA | CTC | ATT | GTC | TTT | GAG | GAA | GAA | GAT | GTC | CGT | GAG | AAC | ATC | ATT | 2443 |
| Glu | Pro | Leu | Ile | Val | Phe | Glu | Glu | Glu | Asp | Val | Arg | Glu | Asn | Ile | Ile |     |
|     |     |     |     | 650 |     |     |     |     | 655 |     |     |     |     | 660 |     |     |
| ACT | TAT | GAT | GAT | GAA | GGG | GGT | GGG | GAA | GAA | GAC | ACA | GAA | GCC | TTT | GAT | 2491 |
| Thr | Tyr | Asp | Asp | Glu | Gly | Gly | Gly | Glu | Glu | Asp | Thr | Glu | Ala | Phe | Asp |     |
|     |     |     | 665 |     |     |     |     | 670 |     |     |     |     | 675 |     |     |     |
| ATT | GCC | ACC | CTC | CAG | AAT | CCT | GAT | GGT | ATC | AAT | GGA | TTT | ATC | CCC | CGC | 2539 |
| Ile | Ala | Thr | Leu | Gln | Asn | Pro | Asp | Gly | Ile | Asn | Gly | Phe | Ile | Pro | Arg |     |
|     |     | 680 |     |     |     |     | 685 |     |     |     |     | 690 |     |     |     |     |
| AAA | GAC | ATC | AAA | CCT | GAG | TAT | CAG | TAC | ATG | CCT | AGA | CCT | GGG | CTC | CGG | 2587 |
| Lys | Asp | Ile | Lys | Pro | Glu | Tyr | Gln | Tyr | Met | Pro | Arg | Pro | Gly | Leu | Arg |     |
| 695 |     |     |     |     | 700 |     |     |     |     |     | 705 |     |     |     |     |     |
| CCA | GCG | CCC | AAC | AGC | GTG | GAT | GTC | GAT | GAC | TTC | ATC | AAC | ACG | AGA | ATA | 2635 |
| Pro | Ala | Pro | Asn | Ser | Val | Asp | Val | Asp | Asp | Phe | Ile | Asn | Thr | Arg | Ile |     |
| 710 |     |     |     |     | 715 |     |     |     |     | 720 |     |     |     |     | 725 |     |
| CAG | GAG | GCA | GAC | AAT | GAC | CCC | ACG | GCT | CCT | CCT | TAT | GAC | TCC | ATT | CAA | 2683 |
| Gln | Glu | Ala | Asp | Asn | Asp | Pro | Thr | Ala | Pro | Pro | Tyr | Asp | Ser | Ile | Gln |     |
|     |     |     |     | 730 |     |     |     |     | 735 |     |     |     |     | 740 |     |     |
| ATC | TAC | GGT | TAT | GAA | GGC | AGG | GGC | TCA | GTG | GCC | GGG | TCC | CTG | AGC | TCC | 2731 |
| Ile | Tyr | Gly | Tyr | Glu | Gly | Arg | Gly | Ser | Val | Ala | Gly | Ser | Leu | Ser | Ser |     |
|     |     |     | 745 |     |     |     |     | 750 |     |     |     |     | 755 |     |     |     |
| CTA | GAG | TCG | GCC | ACC | ACA | GAT | TCA | GAC | TTG | GAC | TAT | GAT | TAT | CTA | CAG | 2779 |
| Leu | Glu | Ser | Ala | Thr | Thr | Asp | Ser | Asp | Leu | Asp | Tyr | Asp | Tyr | Leu | Gln |     |
|     |     |     | 760 |     |     |     |     | 765 |     |     |     |     | 770 |     |     |     |
| AAC | TGG | GGA | CCT | CGT | TTT | AAG | AAA | CTA | GCA | GAT | TTG | TAT | GGT | TCC | AAA | 2827 |
| Asn | Trp | Gly | Pro | Arg | Phe | Lys | Lys | Leu | Ala | Asp | Leu | Tyr | Gly | Ser | Lys |     |
|     | 775 |     |     |     |     |     | 780 |     |     |     |     | 785 |     |     |     |     |
| GAC | ACT | TTT | GAT | GAC | GAT | TCT | TAACAATAAC | GATACAAATT | TGGCCTTAAG | | | | | | | 2878 |
| Asp | Thr | Phe | Asp | Asp | Asp | Ser |     |     |     |     |     |     |     |     |     |     |
| 790 |     |     |     |     | 795 |     |     |     |     |     |     |     |     |     |     |     |

| | | | | |
|---|---|---|---|---|
| AACTGTGTCT | GGCGTTCTCA | AGAATCTAGA | AGATGTGTAA | ACAGGTATTT | TTTTAAATCA | 2938 |
| AGGAAAGGCT | CATTTAAAAC | AGGCAAAGTT | TTACAGAGAG | GATACATTTA | ATAAAACTGC | 2998 |
| GAGGACATCA | AAGTGGTAAA | TACTGTGAAA | TACCTTTTCT | CACAAAAAGG | CAAATATTGA | 3058 |
| AGTTGTTTAT | CAACTTCGCT | AGAAAAAAAA | AACACTTGGC | ATACAAAATA | TTTAAGTGAA | 3118 |
| GGAGAAGTCT | AACGCTGAAC | TGACAATGAA | GGGAAATTGT | TTATGTGTTA | TGAACATCCA | 3178 |
| AGTCTTTCTT | CTTTTTTAAG | TTGTCAAAGA | AGCTTCCACA | AAATTAGAAA | GGACAACAGT | 3238 |
| TCTGAGCTGT | AATTTCGCCT | TAAACTCTGG | ACACTCTATA | TGTAGTGCAT | TTTTAAACTT | 3298 |
| GAAATATATA | ATATTCAGCC | AGCTTAAACC | CATACAATGT | ATGTACAATA | CAATGTACAA | 3358 |
| TTATGTCTCT | TGAGCATCAA | TCTTGTTACT | GCTGATTCTT | GTAAATCTTT | TTGCTTCTAC | 3418 |
| TTTCATCTTA | AACTAATACG | TGCCAGATAT | AACTGTCTTG | TTTCAGTGAG | AGACGCCCTA | 3478 |
| TTTCTATGTC | ATTTTTAATG | TATCTATTTG | TACAATTTTA | AAGTTCTTAT | TTTAGTATAC | 3538 |
| ATATAAATAT | CAGTATTCTG | ACATGTAAGA | AAATGTTACG | GCATCACACT | TATATTTTAT | 3598 |
| GAACATTGTA | CTGTTGCTTT | AATATGAGCT | TCAATATAAG | AAGCAATCTT | TGAAATAAAA | 3658 |
| AAAGATTTTT | TTTAAAAAAA | AAGGAGATCT | ACAGGCCTGT | AGATCTCCGA | ATTC | 3712 |

( 2 ) INFORMATION FOR SEQ ID NO:4:

( i ) SEQUENCE CHARACTERISTICS:
( A ) LENGTH: 796 amino acids
( B ) TYPE: amino acid (D) TOPOLOGY: linear (ii) MOLECULE TYPE: protein (xi) SEQUENCE DESCRIPTION: SEQ ID NO:4:

| Met | Lys | Glu | Asn | Tyr | Cys | Leu | Gln | Ala | Ala | Leu | Val | Cys | Leu | Gly | Met |
|---|---|---|---|---|---|---|---|---|---|---|---|---|---|---|---|
| 1 | | | | 5 | | | | | 10 | | | | | | 15 |

| Leu | Cys | His | Ser | His | Ala | Phe | Ala | Pro | Glu | Arg | Arg | Gly | His | Leu | Arg |
|---|---|---|---|---|---|---|---|---|---|---|---|---|---|---|---|
| | | | 20 | | | | | 25 | | | | | 30 | | |

| Pro | Ser | Phe | His | Gly | His | His | Glu | Lys | Gly | Lys | Glu | Gly | Gln | Val | Leu |
|---|---|---|---|---|---|---|---|---|---|---|---|---|---|---|---|
| | | 35 | | | | | 40 | | | | | 45 | | | |

| Gln | Arg | Ser | Lys | Arg | Gly | Trp | Val | Trp | Asn | Gln | Phe | Phe | Val | Ile | Glu |
|---|---|---|---|---|---|---|---|---|---|---|---|---|---|---|---|
| | 50 | | | | | | 55 | | | | | 60 | | | |

| Glu | Tyr | Thr | Gly | Pro | Asp | Pro | Val | Leu | Val | Gly | Arg | Leu | His | Ser | Asp |
|---|---|---|---|---|---|---|---|---|---|---|---|---|---|---|---|
| 65 | | | | | 70 | | | | | 75 | | | | | 80 |

| Ile | Asp | Ser | Gly | Asp | Gly | Asn | Ile | Lys | Tyr | Ile | Leu | Ser | Gly | Glu | Gly |
|---|---|---|---|---|---|---|---|---|---|---|---|---|---|---|---|
| | | | | 85 | | | | | 90 | | | | | 95 | |

| Ala | Gly | Thr | Ile | Phe | Val | Ile | Asp | Asp | Lys | Ser | Gly | Asn | Ile | His | Ala |
|---|---|---|---|---|---|---|---|---|---|---|---|---|---|---|---|
| | | | 100 | | | | | 105 | | | | | 110 | | |

| Thr | Lys | Thr | Leu | Asp | Arg | Glu | Glu | Arg | Ala | Gln | Tyr | Thr | Leu | Met | Ala |
|---|---|---|---|---|---|---|---|---|---|---|---|---|---|---|---|
| | | 115 | | | | | 120 | | | | | 125 | | | |

| Gln | Ala | Val | Asp | Arg | Asp | Thr | Asn | Arg | Pro | Leu | Glu | Pro | Pro | Ser | Glu |
|---|---|---|---|---|---|---|---|---|---|---|---|---|---|---|---|
| | 130 | | | | | 135 | | | | | 140 | | | | |

| Phe | Ile | Val | Lys | Val | Gln | Asp | Ile | Asn | Asp | Asn | Pro | Pro | Glu | Phe | Leu |
|---|---|---|---|---|---|---|---|---|---|---|---|---|---|---|---|
| 145 | | | | | 150 | | | | | 155 | | | | | 160 |

| His | Glu | Thr | Tyr | His | Ala | Asn | Val | Pro | Glu | Arg | Ser | Asn | Val | Gly | Thr |
|---|---|---|---|---|---|---|---|---|---|---|---|---|---|---|---|
| | | | | 165 | | | | | 170 | | | | | 175 | |

| Ser | Val | Ile | Gln | Val | Thr | Ala | Ser | Asp | Ala | Asp | Pro | Thr | Tyr | Gly |
|---|---|---|---|---|---|---|---|---|---|---|---|---|---|---|
| | | | 180 | | | | | 185 | | | | | 190 | |

| Asn | Ser | Ala | Lys | Leu | Val | Tyr | Ser | Ile | Leu | Glu | Gly | Gln | Pro | Tyr | Phe |
|---|---|---|---|---|---|---|---|---|---|---|---|---|---|---|---|
| | | 195 | | | | | 200 | | | | | 205 | | | |

| Ser | Val | Glu | Ala | Gln | Thr | Gly | Ile | Ile | Arg | Thr | Ala | Leu | Pro | Asn | Met |
|---|---|---|---|---|---|---|---|---|---|---|---|---|---|---|---|
| | 210 | | | | | 215 | | | | | 220 | | | | |

| Asp | Arg | Glu | Ala | Lys | Glu | Glu | Tyr | His | Val | Val | Ile | Gln | Ala | Lys | Asp |
|---|---|---|---|---|---|---|---|---|---|---|---|---|---|---|---|
| 225 | | | | | 230 | | | | | 235 | | | | | 240 |

| Met | Gly | Gly | His | Met | Gly | Gly | Leu | Ser | Gly | Thr | Thr | Lys | Val | Thr | Ile |
|---|---|---|---|---|---|---|---|---|---|---|---|---|---|---|---|
| | | | | 245 | | | | | 250 | | | | | 255 | |

| Thr | Leu | Thr | Asp | Val | Asn | Asp | Asn | Pro | Pro | Lys | Phe | Pro | Gln | Ser | Val |
|---|---|---|---|---|---|---|---|---|---|---|---|---|---|---|---|
| | | | 260 | | | | | 265 | | | | | 270 | | |

| Tyr | Gln | Ile | Ser | Val | Ser | Glu | Ala | Ala | Val | Pro | Gly | Glu | Glu | Val | Gly |
|---|---|---|---|---|---|---|---|---|---|---|---|---|---|---|---|
| | | 275 | | | | | 280 | | | | | 285 | | | |

| Arg | Val | Lys | Ala | Lys | Asp | Pro | Asp | Ile | Gly | Glu | Asn | Gly | Leu | Val | Thr |
|---|---|---|---|---|---|---|---|---|---|---|---|---|---|---|---|
| | 290 | | | | | 295 | | | | | 300 | | | | |

| Tyr | Asn | Ile | Val | Asp | Gly | Asp | Gly | Met | Glu | Ser | Phe | Glu | Ile | Thr | Thr |
|---|---|---|---|---|---|---|---|---|---|---|---|---|---|---|---|
| 305 | | | | | 310 | | | | | 315 | | | | | 320 |

| Asp | Tyr | Glu | Thr | Gln | Glu | Gly | Val | Ile | Lys | Leu | Lys | Lys | Pro | Val | Asp |
|---|---|---|---|---|---|---|---|---|---|---|---|---|---|---|---|
| | | | | 325 | | | | | 330 | | | | | 335 | |

| Phe | Glu | Thr | Lys | Arg | Ala | Tyr | Ser | Leu | Lys | Val | Glu | Ala | Ala | Asn | Val |
|---|---|---|---|---|---|---|---|---|---|---|---|---|---|---|---|
| | | | 340 | | | | | 345 | | | | | 350 | | |

| His | Ile | Asp | Pro | Lys | Phe | Ile | Ser | Asn | Gly | Pro | Phe | Lys | Asp | Thr | Val |
|---|---|---|---|---|---|---|---|---|---|---|---|---|---|---|---|
| | | 355 | | | | | 360 | | | | | 365 | | | |

| Thr | Val | Lys | Ile | Ala | Val | Glu | Asp | Ala | Asp | Glu | Pro | Pro | Met | Phe | Leu |
|---|---|---|---|---|---|---|---|---|---|---|---|---|---|---|---|
| | 370 | | | | | 375 | | | | | 380 | | | | |

| Ala | Pro | Ser | Tyr | Ile | His | Glu | Val | Gln | Glu | Asn | Ala | Ala | Ala | Gly | Thr |
|---|---|---|---|---|---|---|---|---|---|---|---|---|---|---|---|
| 385 | | | | | 390 | | | | | 395 | | | | | 400 |

-continued

| | | | | | | | | | | | | | | |
|---|---|---|---|---|---|---|---|---|---|---|---|---|---|---|
| Val | Val | Gly | Arg | Val<br>405 | His | Ala | Lys | Asp | Pro<br>410 | Asp | Ala | Ala | Asn | Ser<br>415 | Pro |
| Ile | Arg | Tyr | Ser<br>420 | Ile | Asp | Arg | His | Thr<br>425 | Asp | Leu | Asp | Arg | Phe<br>430 | Phe | Thr |
| Ile | Asn | Pro<br>435 | Glu | Asp | Gly | Phe | Ile<br>440 | Lys | Thr | Thr | Lys | Pro<br>445 | Leu | Asp | Arg |
| Glu | Glu<br>450 | Thr | Ala | Trp | Leu | Asn<br>455 | Ile | Thr | Val | Phe | Ala<br>460 | Ala | Glu | Ile | His |
| Asn<br>465 | Arg | His | Gln | Glu | Lys<br>470 | Val | Pro | Val | Ala | Ile<br>475 | Arg | Val | Leu | Asp<br>480 |
| Val | Asn | Asp | Asn | Ala<br>485 | Pro | Lys | Phe | Ala | Ala<br>490 | Pro | Tyr | Glu | Gly | Phe<br>495 | Ile |
| Cys | Glu | Ser | Asp<br>500 | Gln | Thr | Lys | Pro | Leu<br>505 | Ser | Asn | Gln | Pro | Ile<br>510 | Val | Thr |
| Ile | Ser | Ala<br>515 | Asp | Asp | Lys | Asp | Asp<br>520 | Thr | Ala | Asn | Gly | Pro<br>525 | Arg | Phe | Ile |
| Phe | Ser<br>530 | Leu | Pro | Pro | Glu | Ile<br>535 | Ile | His | Asn | Pro | Asn<br>540 | Phe | Thr | Val | Arg |
| Asp<br>545 | Asn | Arg | Asp | Asn | Thr<br>550 | Ala | Gly | Val | Tyr | Ala<br>555 | Arg | Arg | Gly | Gly | Phe<br>560 |
| Ser | Arg | Gln | Lys | Gln<br>565 | Asp | Leu | Tyr | Leu<br>570 | Pro | Ile | Val | Ile | Ser<br>575 | Asp |
| Gly | Gly | Ile | Pro<br>580 | Pro | Met | Ser | Ser | Thr<br>585 | Asn | Thr | Leu | Thr | Ile<br>590 | Lys | Val |
| Cys | Gly | Cys<br>595 | Asp | Val | Asn | Gly | Ala<br>600 | Leu | Leu | Ser | Cys<br>605 | Asn | Ala | Glu | Ala |
| Tyr | Ile<br>610 | Leu | Asn | Ala | Gly | Leu<br>615 | Ser | Thr | Gly | Ala | Leu<br>620 | Ile | Ala | Ile | Leu |
| Ala<br>625 | Cys | Ile | Val | Ile<br>630 | Leu | Leu | Val | Ile<br>635 | Val | Val | Leu | Phe | Val | Thr | Leu<br>640 |
| Arg | Arg | Gln | Lys | Lys<br>645 | Glu | Pro | Leu | Ile<br>650 | Val | Phe | Glu | Glu | Glu<br>655 | Asp | Val |
| Arg | Glu | Asn | Ile<br>660 | Ile | Thr | Tyr | Asp | Asp<br>665 | Glu | Gly | Gly | Gly | Glu<br>670 | Glu | Asp |
| Thr | Glu | Ala<br>675 | Phe | Asp | Ile | Ala | Thr<br>680 | Leu | Gln | Asn | Pro | Asp<br>685 | Gly | Ile | Asn |
| Gly | Phe<br>690 | Ile | Pro | Arg | Lys | Asp<br>695 | Ile | Lys | Pro | Glu | Tyr<br>700 | Gln | Tyr | Met | Pro |
| Arg<br>705 | Pro | Gly | Leu | Arg | Pro<br>710 | Ala | Pro | Asn | Ser | Val<br>715 | Asp | Val | Asp | Asp<br>720 | Phe |
| Ile | Asn | Thr | Arg | Ile<br>725 | Gln | Glu | Ala | Asp | Asn<br>730 | Asp | Pro | Thr | Ala | Pro<br>735 | Pro |
| Tyr | Asp | Ser | Ile<br>740 | Gln | Ile | Tyr | Gly | Tyr<br>745 | Glu | Gly | Arg | Gly | Ser<br>750 | Val | Ala |
| Gly | Ser | Leu<br>755 | Ser | Ser | Leu | Glu | Ser<br>760 | Ala | Thr | Thr | Asp | Ser<br>765 | Asp | Leu | Asp |
| Tyr | Asp<br>770 | Tyr | Leu | Gln | Asn | Trp<br>775 | Gly | Pro | Arg | Phe | Lys<br>780 | Lys | Leu | Ala | Asp |
| Leu<br>785 | Tyr | Gly | Ser | Lys | Asp<br>790 | Thr | Phe | Asp | Asp | Asp<br>795 | Ser | | | | |

( 2 ) INFORMATION FOR SEQ ID NO:5:

( i ) SEQUENCE CHARACTERISTICS:

-continued (A) LENGTH: 3914 base pairs
(B) TYPE: nucleic acid
(C) STRANDEDNESS: double
(D) TOPOLOGY: linear (i i) MOLECULE TYPE: cDNA to mRNA (i x) FEATURE:
(A) NAME/KEY: CDS
(B) LOCATION: 491..2569

(x i) SEQUENCE DESCRIPTION: SEQ ID NO:5:

```
GAATTCGGAG ATCTACAGGC CCGCGACGCT CCCCTCAGCT GGCGGCGGCC GCGGAGAGAT      60

GCCGCGGGGG CCGCTCGCAG CCGCCGCTGA CTTGTGAATG GGACCGGGAC TGGGGCCGGG     120

ACTGACACCG CAGCGCTTGC CCTGCGCCAG GGACTGGCGG CTCGGAGGTT GCGTCCACCC     180

TCAAGGGCCC CAGAAATCAC TGTGTTTTCA GCTCAGCGGC CCTGTGACAT TCCTTCGTGT     240

TGTCATTTGT TGAGTGACCA ATCAGATGGG TGGAGTGTGT TACAGAAATT GGCAGCAAGT     300

ATCCAATGGG TGAAGAAGAA GCTAACTGGG GACGTGGGCA GCCCTGACGT GATGAGCTCA     360

ACCAGCAGAG ACATTCCATC CCAAGAGAGG TCTGCGTGAC GCGTCCGGGA GGCCACCCTC     420

AGCAAGACCA CCGTACAGTT GGTGGAAGGG GTGACAGCTG CATTCTCCTG TGCCTACCAC     480
```

| | | | | | | | | | | | | | | | |
|---|---|---|---|---|---|---|---|---|---|---|---|---|---|---|---|
|GTAACCAAAA|ATG|AAG|GAG|AAC|TAC|TGT|TTA|CAA|GCC|GCC|CTG|GTG|TGC| |529|
| |Met|Lys|Glu|Asn|Tyr|Cys|Leu|Gln|Ala|Ala|Leu|Val|Cys| | |
| |1| | | |5| | | | |10| | | | | |
|CTG|GGC|ATG|CTG|TGC|CAC|AGC|CAT|GCC|TTT|GCC|CCA|GAG|CGG|CGG|GGG|577|
|Leu|Gly|Met|Leu|Cys|His|Ser|His|Ala|Phe|Ala|Pro|Glu|Arg|Arg|Gly| |
| |15| | | |20| | | |25| | | | | | |
|CAC|CTG|CGG|CCC|TCC|TTC|CAT|GGG|CAC|CAT|GAG|AAG|GGC|AAG|GAG|GGG|625|
|His|Leu|Arg|Pro|Ser|Phe|His|Gly|His|His|Glu|Lys|Gly|Lys|Glu|Gly| |
| |30| | | |35| | | |40| | | | | |45| |
|CAG|GTG|CTA|CAG|CGC|TCC|AAG|CGT|GGC|TGG|GTC|TGG|AAC|CAG|TTC|TTC|673|
|Gln|Val|Leu|Gln|Arg|Ser|Lys|Arg|Gly|Trp|Val|Trp|Asn|Gln|Phe|Phe| |
| | | | |50| | | |55| | | | |60| | |
|GTG|ATA|GAG|GAG|TAC|ACC|GGG|CCT|GAC|CCC|GTG|CTT|GTG|GGC|AGG|CTT|721|
|Val|Ile|Glu|Glu|Tyr|Thr|Gly|Pro|Asp|Pro|Val|Leu|Val|Gly|Arg|Leu| |
| | | |65| | | |70| | | |75| | | | |
|CAT|TCA|GAT|ATT|GAC|TCT|GGT|GAT|GGG|AAC|ATT|AAA|TAC|ATT|CTC|TCA|769|
|His|Ser|Asp|Ile|Asp|Ser|Gly|Asp|Gly|Asn|Ile|Lys|Tyr|Ile|Leu|Ser| |
| | |80| | | |85| | | |90| | | | | |
|GGG|GAA|GGA|GCT|GGA|ACC|ATT|TTT|GTG|ATT|GAT|GAC|AAA|TCA|GGG|AAC|817|
|Gly|Glu|Gly|Ala|Gly|Thr|Ile|Phe|Val|Ile|Asp|Asp|Lys|Ser|Gly|Asn| |
| |95| | | |100| | | |105| | | | | | |
|ATT|CAT|GCC|ACC|AAG|ACG|TTG|GAT|CGA|GAA|GAG|AGA|GCC|CAG|TAC|ACG|865|
|Ile|His|Ala|Thr|Lys|Thr|Leu|Asp|Arg|Glu|Glu|Arg|Ala|Gln|Tyr|Thr| |
|110| | | |115| | | |120| | | | |125| | |
|TTG|ATG|GCT|CAG|GCG|GTG|GAC|AGG|GAC|ACC|AAT|CGG|CCA|CTG|GAG|CCA|913|
|Leu|Met|Ala|Gln|Ala|Val|Asp|Arg|Asp|Thr|Asn|Arg|Pro|Leu|Glu|Pro| |
| | | |130| | | |135| | | |140| | | | |
|CCG|TCG|GAA|TTC|ATT|GTC|AAG|GTC|CAG|GAC|ATT|AAT|GAC|AAC|CCT|CCG|961|
|Pro|Ser|Glu|Phe|Ile|Val|Lys|Val|Gln|Asp|Ile|Asn|Asp|Asn|Pro|Pro| |
| | | |145| | | |150| | | |155| | | | |
|GAG|TTC|CTG|CAC|GAG|ACC|TAT|CAT|GCC|AAC|GTG|CCT|GAG|AGG|TCC|AAT|1009|
|Glu|Phe|Leu|His|Glu|Thr|Tyr|His|Ala|Asn|Val|Pro|Glu|Arg|Ser|Asn| |
| | |160| | | |165| | | |170| | | | | |
|GTG|GGA|ACG|TCA|GTA|ATC|CAG|GTG|ACA|GCT|TCA|GAT|GCA|GAT|GAC|CCC|1057|
|Val|Gly|Thr|Ser|Val|Ile|Gln|Val|Thr|Ala|Ser|Asp|Ala|Asp|Asp|Pro| |
| |175| | | |180| | | |185| | | | | | |
|ACT|TAT|GGA|AAT|AGC|GCC|AAG|TTA|GTG|TAC|AGT|ATC|CTC|GAA|GGA|CAA|1105|
|Thr|Tyr|Gly|Asn|Ser|Ala|Lys|Leu|Val|Tyr|Ser|Ile|Leu|Glu|Gly|Gln| |
|190| | | |195| | | |200| | | | |205| | |

| | | | | | | | | | | | | | | | | |
|---|---|---|---|---|---|---|---|---|---|---|---|---|---|---|---|---|
| CCC | TAT | TTT | TCG | GTG | GAA | GCA | CAG | ACA | GGT | ATC | ATC | AGA | ACA | GCC | CTA | 1153 |
| Pro | Tyr | Phe | Ser | Val | Glu | Ala | Gln | Thr | Gly | Ile | Ile | Arg | Thr | Ala | Leu | |
| | | | | 210 | | | | 215 | | | | | 220 | | | |
| CCC | AAC | ATG | GAC | AGG | GAG | GCC | AAG | GAG | GAG | TAC | CAC | GTG | GTG | ATC | CAG | 1201 |
| Pro | Asn | Met | Asp | Arg | Glu | Ala | Lys | Glu | Glu | Tyr | His | Val | Val | Ile | Gln | |
| | | | 225 | | | | | 230 | | | | | 235 | | | |
| GCC | AAG | GAC | ATG | GGT | GGA | CAT | ATG | GGC | GGA | CTC | TCA | GGG | ACA | ACC | AAA | 1249 |
| Ala | Lys | Asp | Met | Gly | Gly | His | Met | Gly | Gly | Leu | Ser | Gly | Thr | Thr | Lys | |
| | | | 240 | | | | | 245 | | | | | 250 | | | |
| GTG | ACG | ATC | ACA | CTG | ACC | GAT | GTC | AAT | GAC | AAC | CCA | CCA | AAG | TTT | CCG | 1297 |
| Val | Thr | Ile | Thr | Leu | Thr | Asp | Val | Asn | Asp | Asn | Pro | Pro | Lys | Phe | Pro | |
| | | 255 | | | | | 260 | | | | | 265 | | | | |
| CAG | AGC | GTA | TAC | CAG | ATA | TCT | GTG | TCA | GAA | GCA | GCC | GTC | CCT | GGG | GAG | 1345 |
| Gln | Ser | Val | Tyr | Gln | Ile | Ser | Val | Ser | Glu | Ala | Ala | Val | Pro | Gly | Glu | |
| 270 | | | | | 275 | | | | | 280 | | | | | 285 | |
| GAA | GTA | GGA | AGA | GTG | AAA | GCT | AAA | GAT | CCA | GAC | ATT | GGA | GAA | AAT | GGC | 1393 |
| Glu | Val | Gly | Arg | Val | Lys | Ala | Lys | Asp | Pro | Asp | Ile | Gly | Glu | Asn | Gly | |
| | | | | 290 | | | | | 295 | | | | | 300 | | |
| TTA | GTC | ACA | TAC | AAT | ATT | GTT | GAT | GGA | GAT | GGT | ATG | GAA | TCG | TTT | GAA | 1441 |
| Leu | Val | Thr | Tyr | Asn | Ile | Val | Asp | Gly | Asp | Gly | Met | Glu | Ser | Phe | Glu | |
| | | | 305 | | | | | 310 | | | | | 315 | | | |
| ATC | ACA | ACG | GAC | TAT | GAA | ACA | CAG | GAG | GGG | GTG | ATA | AAG | CTG | AAA | AAG | 1489 |
| Ile | Thr | Thr | Asp | Tyr | Glu | Thr | Gln | Glu | Gly | Val | Ile | Lys | Leu | Lys | Lys | |
| | | 320 | | | | | 325 | | | | | 330 | | | | |
| CCT | GTA | GAT | TTT | GAA | ACC | AAA | AGA | GCC | TAT | AGC | TTG | AAG | GTA | GAG | GCA | 1537 |
| Pro | Val | Asp | Phe | Glu | Thr | Lys | Arg | Ala | Tyr | Ser | Leu | Lys | Val | Glu | Ala | |
| | 335 | | | | | 340 | | | | | 345 | | | | | |
| GCC | AAC | GTG | CAC | ATC | GAC | CCG | AAG | TTT | ATC | AGC | AAT | GGC | CCT | TTC | AAG | 1585 |
| Ala | Asn | Val | His | Ile | Asp | Pro | Lys | Phe | Ile | Ser | Asn | Gly | Pro | Phe | Lys | |
| 350 | | | | | 355 | | | | | 360 | | | | | 365 | |
| GAC | ACT | GTG | ACC | GTC | AAG | ATC | GCA | GTA | GAA | GAT | GCT | GAT | GAG | CCC | CCT | 1633 |
| Asp | Thr | Val | Thr | Val | Lys | Ile | Ala | Val | Glu | Asp | Ala | Asp | Glu | Pro | Pro | |
| | | | | 370 | | | | | 375 | | | | | 380 | | |
| ATG | TTC | TTG | GCC | CCA | AGT | TAC | ATC | CAC | GAA | GTC | CAA | GAA | AAT | GCA | GCT | 1681 |
| Met | Phe | Leu | Ala | Pro | Ser | Tyr | Ile | His | Glu | Val | Gln | Glu | Asn | Ala | Ala | |
| | | | 385 | | | | | 390 | | | | | 395 | | | |
| GCT | GGC | ACC | GTG | GTT | GGG | AGA | GTG | CAT | GCC | AAA | GAC | CCT | GAT | GCT | GCC | 1729 |
| Ala | Gly | Thr | Val | Val | Gly | Arg | Val | His | Ala | Lys | Asp | Pro | Asp | Ala | Ala | |
| | | 400 | | | | | 405 | | | | | 410 | | | | |
| AAC | AGC | CCG | ATA | AGG | TAT | TCC | ATC | GAT | CGT | CAC | ACT | GAC | CTC | GAC | AGA | 1777 |
| Asn | Ser | Pro | Ile | Arg | Tyr | Ser | Ile | Asp | Arg | His | Thr | Asp | Leu | Asp | Arg | |
| | 415 | | | | | 420 | | | | | 425 | | | | | |
| TTT | TTC | ACT | ATT | AAT | CCA | GAG | GAT | GGT | TTT | ATT | AAA | ACT | ACA | AAA | CCT | 1825 |
| Phe | Phe | Thr | Ile | Asn | Pro | Glu | Asp | Gly | Phe | Ile | Lys | Thr | Thr | Lys | Pro | |
| 430 | | | | | 435 | | | | | 440 | | | | | 445 | |
| CTG | GAT | AGA | GAG | GAA | ACA | GCC | TGG | CTC | AAC | ATC | ACT | GTC | TTT | GCA | GCA | 1873 |
| Leu | Asp | Arg | Glu | Glu | Thr | Ala | Trp | Leu | Asn | Ile | Thr | Val | Phe | Ala | Ala | |
| | | | | 450 | | | | | 455 | | | | | 460 | | |
| GAA | ATC | CAC | AAT | CGG | CAT | CAG | GAA | GCC | AAA | GTC | CCA | GTG | GCC | ATT | AGG | 1921 |
| Glu | Ile | His | Asn | Arg | His | Gln | Glu | Ala | Lys | Val | Pro | Val | Ala | Ile | Arg | |
| | | | 465 | | | | | 470 | | | | | 475 | | | |
| GTC | CTT | GAT | GTC | AAC | GAT | AAT | GCT | CCC | AAG | TTT | GCT | GCC | CCT | TAT | GAA | 1969 |
| Val | Leu | Asp | Val | Asn | Asp | Asn | Ala | Pro | Lys | Phe | Ala | Ala | Pro | Tyr | Glu | |
| | | 480 | | | | | 485 | | | | | 490 | | | | |
| GGT | TTC | ATC | TGT | GAG | AGT | GAT | CAG | ACC | AAG | CCA | CTT | TCC | AAC | CAG | CCA | 2017 |
| Gly | Phe | Ile | Cys | Glu | Ser | Asp | Gln | Thr | Lys | Pro | Leu | Ser | Asn | Gln | Pro | |
| | 495 | | | | | 500 | | | | | 505 | | | | | |
| ATT | GTT | ACA | ATT | AGT | GCA | GAT | GAC | AAG | GAT | GAC | ACG | GCC | AAT | GGA | CCA | 2065 |
| Ile | Val | Thr | Ile | Ser | Ala | Asp | Asp | Lys | Asp | Asp | Thr | Ala | Asn | Gly | Pro | |
| 510 | | | | | 515 | | | | | 520 | | | | | 525 | |

| | | | | | | | | | | | | | | | | |
|---|---|---|---|---|---|---|---|---|---|---|---|---|---|---|---|---|
| AGA | TTT | ATC | TTC | AGC | CTA | CCC | CCT | GAA | ATC | ATT | CAC | AAT | CCA | AAT | TTC | 2113 |
| Arg | Phe | Ile | Phe | Ser | Leu | Pro | Pro | Glu | Ile | Ile | His | Asn | Pro | Asn | Phe | |
| | | | | 530 | | | | | 535 | | | | | 540 | | |
| ACA | GTC | AGA | GAC | AAC | CGA | GAT | AAC | ACA | GCA | GGC | GTG | TAC | GCC | CGG | CGT | 2161 |
| Thr | Val | Arg | Asp | Asn | Arg | Asp | Asn | Thr | Ala | Gly | Val | Tyr | Ala | Arg | Arg | |
| | | | 545 | | | | | 550 | | | | | 555 | | | |
| GGA | GGG | TTC | AGT | CGG | CAG | AAG | CAG | GAC | TTG | TAC | CTT | CTG | CCC | ATA | GTG | 2209 |
| Gly | Gly | Phe | Ser | Arg | Gln | Lys | Gln | Asp | Leu | Tyr | Leu | Leu | Pro | Ile | Val | |
| | | 560 | | | | | 565 | | | | | 570 | | | | |
| ATC | AGC | GAT | GGC | GGC | ATC | CCG | CCC | ATG | AGT | AGC | ACC | AAC | ACC | CTC | ACC | 2257 |
| Ile | Ser | Asp | Gly | Gly | Ile | Pro | Pro | Met | Ser | Ser | Thr | Asn | Thr | Leu | Thr | |
| | 575 | | | | | 580 | | | | | 585 | | | | | |
| ATC | AAA | GTC | TGC | GGG | TGC | GAC | GTG | AAC | GGG | GCA | CTG | CTC | TCC | TGC | AAC | 2305 |
| Ile | Lys | Val | Cys | Gly | Cys | Asp | Val | Asn | Gly | Ala | Leu | Leu | Ser | Cys | Asn | |
| 590 | | | | | 595 | | | | | 600 | | | | | 605 | |
| GCA | GAG | GCC | TAC | ATT | CTG | AAC | GCC | GGC | CTG | AGC | ACA | GGC | GCC | CTG | ATC | 2353 |
| Ala | Glu | Ala | Tyr | Ile | Leu | Asn | Ala | Gly | Leu | Ser | Thr | Gly | Ala | Leu | Ile | |
| | | | | 610 | | | | | 615 | | | | | 620 | | |
| GCC | ATC | CTC | GCC | TGC | ATC | GTC | ATT | CTC | CTG | GGT | TGC | CCA | AGC | TTA | ATG | 2401 |
| Ala | Ile | Leu | Ala | Cys | Ile | Val | Ile | Leu | Leu | Gly | Cys | Pro | Ser | Leu | Met | |
| | | | 625 | | | | | 630 | | | | | 635 | | | |
| GAA | CCC | CCC | TCT | CCC | AGG | GAA | GAC | ATG | AGA | TTG | CTT | TAT | CTG | GGC | TTC | 2449 |
| Glu | Pro | Pro | Ser | Pro | Arg | Glu | Asp | Met | Arg | Leu | Leu | Tyr | Leu | Gly | Phe | |
| | | 640 | | | | | 645 | | | | | 650 | | | | |
| CAG | CTG | ATG | CTA | TTT | TCC | TAT | GTT | AAA | GTA | AAC | AGA | AGA | TTT | TGT | CTT | 2497 |
| Gln | Leu | Met | Leu | Phe | Ser | Tyr | Val | Lys | Val | Asn | Arg | Arg | Phe | Cys | Leu | |
| | 655 | | | | | 660 | | | | | 665 | | | | | |
| CTG | GGG | GTC | TTT | ATA | AAA | CTT | CCT | TTC | CTC | TAT | GTG | GTG | GCT | ACA | GAG | 2545 |
| Leu | Gly | Val | Phe | Ile | Lys | Leu | Pro | Phe | Leu | Tyr | Val | Val | Ala | Thr | Glu | |
| 670 | | | | | 675 | | | | | 680 | | | | | 685 | |
| AGT | CCA | ACC | ACA | CTT | ACG | TCA | TTG | TAGTATTGTT | TGTGACCCTG | AGAAGGCAAA | | | | | | 2599 |
| Ser | Pro | Thr | Thr | Leu | Thr | Ser | Leu | | | | | | | | | |
| | | | | 690 | | | | | | | | | | | | |

| | | | | |
|---|---|---|---|---|
| AGAAAGAACC | ACTCATTGTC | TTTGAGGAAG | AAGATGTCCG | TGAGAACATC ATTACTTATG | 2659 |
| ATGATGAAGG | GGGTGGGGAA | GAAGACACAG | AAGCCTTTGA | TATTGCCACC CTCCAGAATC | 2719 |
| CTGATGGTAT | CAATGGATTT | ATCCCCCGCA | AAGACATCAA | ACCTGAGTAT CAGTACATGC | 2779 |
| CTAGACCTGG | GCTCCGGCCA | GCGCCCAACA | GCGTGGATGT | CGATGACTTC ATCAACACGA | 2839 |
| GAATACAGGA | GGCAGACAAT | GACCCCACGG | CTCCTCCTTA | TGACTCCATT CAAATCTACG | 2899 |
| GTTATGAAGG | CAGGGGCTCA | GTGGCCGGGT | CCCTGAGCTC | CTAGAGTCG GCCACCACAG | 2959 |
| ATTCAGACTT | GGACTATGAT | TATCTACAGA | ACTGGGGACC | TCGTTTTAAG AAACTAGCAG | 3019 |
| ATTTGTATGG | TTCCAAAGAC | ACTTTTGATG | ACGATTCTTA | CAATAACGA TACAAATTTG | 3079 |
| GCCTTAAGAA | CTGTGTCTGG | CGTTCTCAAG | AATCTAGAAG | ATGTGTAAAC AGGTATTTTT | 3139 |
| TTAAATCAAG | GAAAGGCTCA | TTTAAAACAG | GCAAAGTTTT | ACAGAGAGGA TACATTTAAT | 3199 |
| AAAACTGCGA | GGACATCAAA | GTGGTAAATA | CTGTGAAATA | CCTTTTCTCA CAAAAAGGCA | 3259 |
| AATATTGAAG | TTGTTTATCA | ACTTCGCTAG | AAAAAAAAA | CACTTGGCAT ACAAAATATT | 3319 |
| TAAGTGAAGG | AGAAGTCTAA | CGCTGAACTG | ACAATGAAGG | GAAATTGTTT ATGTGTTATG | 3379 |
| AACATCCAAG | TCTTTCTTCT | TTTTTAAGTT | GTCAAAGAAG | CTTCCACAAA ATTAGAAAGG | 3439 |
| ACAACAGTTC | TGAGCTGTAA | TTTCGCCTTA | AACTCTGGAC | ACTCTATATG TAGTGCATTT | 3499 |
| TTAAACTTGA | AATATATAAT | ATTCAGCCAG | CTTAAACCCA | TACAATGTAT GTACAATACA | 3559 |
| ATGTACAATT | ATGTCTCTTG | AGCATCAATC | TTGTTACTGC | TGATTCTTGT AAATCTTTTT | 3619 |
| GCTTCTACTT | TCATCTTAAA | CTAATACGTG | CCAGATATAA | CTGTCTTGTT TCAGTGAGAG | 3679 |

```
ACGCCCTATT  TCTATGTCAT  TTTTAATGTA  TCTATTTGTA  CAATTTTAAA  GTTCTTATTT      3739

TAGTATACAT  ATAAATATCA  GTATTCTGAC  ATGTAAGAAA  ATGTTACGGC  ATCACACTTA      3799

TATTTTATGA  ACATTGTACT  GTTGCTTTAA  TATGAGCTTC  AATATAAGAA  GCAATCTTTG      3859

AAATAAAAAA  AGATTTTTTT  TTCGGAGATC  TACAGGCCTG  TAGATCTCCG  AATTC           3914
```

( 2 ) INFORMATION FOR SEQ ID NO:6:

( i ) SEQUENCE CHARACTERISTICS:
        ( A ) LENGTH: 693 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Lys  Glu  Asn  Tyr  Cys  Leu  Gln  Ala  Ala  Leu  Val  Cys  Leu  Gly  Met
 1              5                        10                            15

Leu  Cys  His  Ser  His  Ala  Phe  Ala  Pro  Glu  Arg  Arg  Gly  His  Leu  Arg
                20                        25                        30

Pro  Ser  Phe  His  Gly  His  His  Glu  Lys  Gly  Lys  Glu  Gly  Gln  Val  Leu
               35                        40                        45

Gln  Arg  Ser  Lys  Arg  Gly  Trp  Val  Trp  Asn  Gln  Phe  Phe  Val  Ile  Glu
     50                        55                        60

Glu  Tyr  Thr  Gly  Pro  Asp  Pro  Val  Leu  Val  Gly  Arg  Leu  His  Ser  Asp
 65                        70                        75                    80

Ile  Asp  Ser  Gly  Asp  Gly  Asn  Ile  Lys  Tyr  Ile  Leu  Ser  Gly  Glu  Gly
                85                        90                        95

Ala  Gly  Thr  Ile  Phe  Val  Ile  Asp  Asp  Lys  Ser  Gly  Asn  Ile  His  Ala
               100                       105                       110

Thr  Lys  Thr  Leu  Asp  Arg  Glu  Glu  Arg  Ala  Gln  Tyr  Thr  Leu  Met  Ala
               115                       120                       125

Gln  Ala  Val  Asp  Arg  Asp  Thr  Asn  Arg  Pro  Leu  Glu  Pro  Pro  Ser  Glu
     130                       135                       140

Phe  Ile  Val  Lys  Val  Gln  Asp  Ile  Asn  Asp  Asn  Pro  Pro  Glu  Phe  Leu
145                       150                       155                   160

His  Glu  Thr  Tyr  His  Ala  Asn  Val  Pro  Glu  Arg  Ser  Asn  Val  Gly  Thr
               165                       170                       175

Ser  Val  Ile  Gln  Val  Thr  Ala  Ser  Asp  Ala  Asp  Pro  Thr  Tyr  Gly
               180                       185                       190

Asn  Ser  Ala  Lys  Leu  Val  Tyr  Ser  Ile  Leu  Glu  Gly  Gln  Pro  Tyr  Phe
               195                       200                       205

Ser  Val  Glu  Ala  Gln  Thr  Gly  Ile  Ile  Arg  Thr  Ala  Leu  Pro  Asn  Met
     210                       215                       220

Asp  Arg  Glu  Ala  Lys  Glu  Glu  Tyr  His  Val  Val  Ile  Gln  Ala  Lys  Asp
225                       230                       235                   240

Met  Gly  Gly  His  Met  Gly  Gly  Leu  Ser  Gly  Thr  Thr  Lys  Val  Thr  Ile
               245                       250                       255

Thr  Leu  Thr  Asp  Val  Asn  Asp  Asn  Pro  Pro  Lys  Phe  Pro  Gln  Ser  Val
               260                       265                       270

Tyr  Gln  Ile  Ser  Val  Ser  Glu  Ala  Ala  Val  Pro  Gly  Glu  Glu  Val  Gly
               275                       280                       285

Arg  Val  Lys  Ala  Lys  Asp  Pro  Asp  Ile  Gly  Glu  Asn  Gly  Leu  Val  Thr
     290                       295                       300

Tyr  Asn  Ile  Val  Asp  Gly  Asp  Gly  Met  Glu  Ser  Phe  Glu  Ile  Thr  Thr
305                       310                       315                   320
```

| Asp | Tyr | Glu | Thr | Gln | Glu | Gly | Val | Ile | Lys | Leu | Lys | Lys | Pro | Val | Asp |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |
| Phe | Glu | Thr | Lys | Arg | Ala | Tyr | Ser | Leu | Lys | Val | Glu | Ala | Ala | Asn | Val |
|     |     |     | 340 |     |     |     |     | 345 |     |     |     |     | 350 |     |     |
| His | Ile | Asp | Pro | Lys | Phe | Ile | Ser | Asn | Gly | Pro | Phe | Lys | Asp | Thr | Val |
|     |     | 355 |     |     |     |     | 360 |     |     |     |     | 365 |     |     |     |
| Thr | Val | Lys | Ile | Ala | Val | Glu | Asp | Ala | Asp | Glu | Pro | Pro | Met | Phe | Leu |
|     | 370 |     |     |     |     | 375 |     |     |     |     | 380 |     |     |     |     |
| Ala | Pro | Ser | Tyr | Ile | His | Glu | Val | Gln | Glu | Asn | Ala | Ala | Ala | Gly | Thr |
| 385 |     |     |     |     | 390 |     |     |     |     | 395 |     |     |     |     | 400 |
| Val | Val | Gly | Arg | Val | His | Ala | Lys | Asp | Pro | Asp | Ala | Ala | Asn | Ser | Pro |
|     |     |     |     | 405 |     |     |     |     | 410 |     |     |     |     | 415 |     |
| Ile | Arg | Tyr | Ser | Ile | Asp | Arg | His | Thr | Asp | Leu | Asp | Arg | Phe | Phe | Thr |
|     |     |     | 420 |     |     |     |     | 425 |     |     |     |     | 430 |     |     |
| Ile | Asn | Pro | Glu | Asp | Gly | Phe | Ile | Lys | Thr | Thr | Lys | Pro | Leu | Asp | Arg |
|     |     | 435 |     |     |     |     | 440 |     |     |     |     | 445 |     |     |     |
| Glu | Glu | Thr | Ala | Trp | Leu | Asn | Ile | Thr | Val | Phe | Ala | Ala | Glu | Ile | His |
|     | 450 |     |     |     |     | 455 |     |     |     |     | 460 |     |     |     |     |
| Asn | Arg | His | Gln | Glu | Ala | Lys | Val | Pro | Val | Ala | Ile | Arg | Val | Leu | Asp |
| 465 |     |     |     |     | 470 |     |     |     |     | 475 |     |     |     |     | 480 |
| Val | Asn | Asp | Asn | Ala | Pro | Lys | Phe | Ala | Ala | Pro | Tyr | Glu | Gly | Phe | Ile |
|     |     |     |     | 485 |     |     |     |     | 490 |     |     |     |     | 495 |     |
| Cys | Glu | Ser | Asp | Gln | Thr | Lys | Pro | Leu | Ser | Asn | Gln | Pro | Ile | Val | Thr |
|     |     |     | 500 |     |     |     |     | 505 |     |     |     |     | 510 |     |     |
| Ile | Ser | Ala | Asp | Asp | Lys | Asp | Asp | Thr | Ala | Asn | Gly | Pro | Arg | Phe | Ile |
|     |     |     | 515 |     |     |     | 520 |     |     |     |     | 525 |     |     |     |
| Phe | Ser | Leu | Pro | Pro | Glu | Ile | Ile | His | Asn | Pro | Asn | Phe | Thr | Val | Arg |
|     | 530 |     |     |     |     | 535 |     |     |     |     | 540 |     |     |     |     |
| Asp | Asn | Arg | Asp | Asn | Thr | Ala | Gly | Val | Tyr | Ala | Arg | Arg | Gly | Gly | Phe |
| 545 |     |     |     |     | 550 |     |     |     |     | 555 |     |     |     |     | 560 |
| Ser | Arg | Gln | Lys | Gln | Asp | Leu | Tyr | Leu | Leu | Pro | Ile | Val | Ile | Ser | Asp |
|     |     |     |     | 565 |     |     |     |     | 570 |     |     |     |     | 575 |     |
| Gly | Gly | Ile | Pro | Pro | Met | Ser | Ser | Thr | Asn | Thr | Leu | Thr | Ile | Lys | Val |
|     |     |     | 580 |     |     |     |     | 585 |     |     |     |     | 590 |     |     |
| Cys | Gly | Cys | Asp | Val | Asn | Gly | Ala | Leu | Leu | Ser | Cys | Asn | Ala | Glu | Ala |
|     |     | 595 |     |     |     |     | 600 |     |     |     |     | 605 |     |     |     |
| Tyr | Ile | Leu | Asn | Ala | Gly | Leu | Ser | Thr | Gly | Ala | Leu | Ile | Ala | Ile | Leu |
|     |     | 610 |     |     |     |     | 615 |     |     |     |     | 620 |     |     |     |
| Ala | Cys | Ile | Val | Ile | Leu | Leu | Gly | Cys | Pro | Ser | Leu | Met | Glu | Pro | Pro |
| 625 |     |     |     |     | 630 |     |     |     |     | 635 |     |     |     |     | 640 |
| Ser | Pro | Arg | Glu | Asp | Met | Arg | Leu | Leu | Tyr | Leu | Gly | Phe | Gln | Leu | Met |
|     |     |     |     | 645 |     |     |     |     | 650 |     |     |     |     | 655 |     |
| Leu | Phe | Ser | Tyr | Val | Lys | Val | Asn | Arg | Arg | Phe | Cys | Leu | Leu | Gly | Val |
|     |     |     | 660 |     |     |     |     | 665 |     |     |     |     | 670 |     |     |
| Phe | Ile | Lys | Leu | Pro | Phe | Leu | Tyr | Val | Val | Ala | Thr | Glu | Ser | Pro | Thr |
|     |     | 675 |     |     |     |     | 680 |     |     |     |     | 685 |     |     |     |
| Thr | Leu | Thr | Ser | Leu |     |     |     |     |     |     |     |     |     |     |     |
|     | 690 |     |     |     |     |     |     |     |     |     |     |     |     |     |     |

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single (D) TOPOLOGY: linear (i i) MOLECULE TYPE: Other
    (A) DESCRIPTION: linker DNA with sequence complementary to SEQ ID NO: 8, termed "ATOS-1"

(x i) SEQUENCE DESCRIPTION: SEQ ID NO:7:

CTCTTGCTTG AATTCGGACT A      21

(2) INFORMATION FOR SEQ ID NO:8:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (i i) MOLECULE TYPE: Other
    (A) DESCRIPTION: linker DNA with sequence complementary to SEQ ID NO: 7, termed "ATOS-2"

(x i) SEQUENCE DESCRIPTION: SEQ ID NO:8:

TAGTCCGAAT TCAAGCAAGA GCACA      25

(2) INFORMATION FOR SEQ ID NO:9:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: Other
    (A) DESCRIPTION: linker DNA with sequence complementary to SEQ ID NO: 10, termed "ATOS-4"

(x i) SEQUENCE DESCRIPTION: SEQ ID NO:9:

CTCTTGCTTA AGCTTGGACT A      21

(2) INFORMATION FOR SEQ ID NO:10:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (i i) MOLECULE TYPE: Other
    (A) DESCRIPTION: linker DNA with sequence complementary to SEQ ID NO: 9, termed "ATOS-5"

(x i) SEQUENCE DESCRIPTION: SEQ ID NO:10:

TAGTCCAAGC TTAAGCAAGA GCACA      25

(2) INFORMATION FOR SEQ ID NO:11:

(i) SEQUENCE CHARACTERISTICS:
    (A) LENGTH: 15 amino acids
    (B) TYPE: amino acid
    (D) TOPOLOGY: linear (i i) MOLECULE TYPE: Other
    (A) DESCRIPTION: OSF-4.1 (antigen peptide) segment of mouse OSF-4 from 101st to 115th amino acid residue (v i) ORIGINAL SOURCE:
    (A) ORGANISM: Mus musculus (x i) SEQUENCE DESCRIPTION: SEQ ID NO:11:

Phe Val Ile Asp Asp Lys Ser Gly Asn Ile His Ala Thr Lys Thr (2) INFORMATION FOR SEQ ID NO:12:

(i) SEQUENCE CHARACTERISTICS:
        (A) LENGTH: 615 amino acids
        (B) TYPE: amino acid
        (D) TOPOLOGY: linear (ii) MOLECULE TYPE: peptide (xi) SEQUENCE DESCRIPTION: SEQ ID NO:12:

```
Met Lys Glu Asn Tyr Cys Leu Gln Ala Ala Leu Val Cys Leu Met Leu
  1               5                  10                  15

His Ser Ala Phe Ala Glu Arg Arg His Leu Pro Ser Phe His Gly His
             20                  25                  30

His Glu Lys Gly Lys Glu Gly Gln Val Leu Gln Arg Ser Lys Arg Gly
         35                  40                  45

Trp Val Trp Asn Gln Phe Phe Val Ile Glu Glu Tyr Thr Gly Pro Asp
     50                  55                  60

Pro Val Leu Val Gly Arg Leu His Ser Asp Ile Asp Ser Gly Asp Gly
 65                  70                  75                  80

Asn Ile Lys Tyr Ile Leu Ser Gly Glu Gly Ala Gly Thr Ile Phe Val
                 85                  90                  95

Ile Asp Asp Lys Ser Gly Asn Ile His Ala Thr Lys Thr Leu Asp Arg
             100                 105                 110

Glu Glu Arg Ala Gln Tyr Thr Leu Met Ala Gln Ala Val Asp Arg Asp
         115                 120                 125

Thr Asn Arg Pro Leu Glu Pro Pro Ser Glu Phe Ile Val Lys Val Gln
130                 135                 140

Asp Ile Asn Asp Asn Pro Pro Glu Phe Leu His Glu Tyr His Ala Asn
145                 150                 155                 160

Val Pro Glu Arg Ser Asn Val Gly Thr Ser Val Ile Gln Val Thr Ala
                 165                 170                 175

Ser Asp Ala Asp Asp Pro Thr Tyr Gly Asn Ser Ala Lys Leu Val Tyr
             180                 185                 190

Ser Ile Leu Glu Gly Gln Pro Tyr Phe Ser Val Glu Ala Gln Thr Gly
         195                 200                 205

Ile Ile Arg Thr Ala Leu Pro Asn Met Asp Arg Glu Ala Lys Glu Glu
210                 215                 220

Tyr His Val Val Ile Gln Ala Lys Asp Met Gly Gly His Met Gly Gly
225                 230                 235                 240

Leu Ser Gly Thr Thr Lys Val Thr Ile Thr Leu Thr Asp Val Asn Asp
                 245                 250                 255

Asn Pro Pro Lys Phe Pro Gln Ser Val Tyr Gln Ser Val Ser Glu Ala
             260                 265                 270

Ala Val Pro Gly Glu Glu Val Gly Arg Val Lys Ala Lys Asp Pro Asp
         275                 280                 285

Ile Gly Glu Asn Gly Leu Val Thr Tyr Asn Ile Val Asp Gly Asp Gly
     290                 295                 300

Glu Phe Glu Ile Thr Thr Asp Tyr Glu Thr Gln Gly Val Lys Leu Lys
305                 310                 315                 320

Lys Pro Val Asp Phe Glu Thr Lys Arg Ala Tyr Ser Leu Lys Glu Ala
                 325                 330                 335

Ala Asn Val His Ile Asp Pro Lys Phe Ile Ser Asn Gly Pro Phe Lys
             340                 345                 350
```

```
Asp Thr Val Thr Val Lys Ile Val Glu Asp Ala Asp Glu Pro Pro Met
        355             360             365
Phe Leu Ala Pro Ser Tyr Ile His Glu Val Gln Glu Asn Ala Ala Ala
    370             375             380
Gly Thr Val Val Gly Arg Val His Ala Lys Asp Pro Asp Ala Ala Asn
385             390             395                         400
Ser Pro Ile Arg Tyr Ser Ile Asp Arg His Thr Asp Leu Asp Arg Phe
            405             410                     415
Phe Thr Ile Asn Pro Glu Asp Gly Phe Ile Lys Thr Thr Lys Pro Leu
            420             425             430
Asp Arg Glu Glu Thr Ala Trp Leu Asn Ile Val Phe Ala Ala Glu Ile
        435             440             445
His Asn Arg His Gln Glu Lys Val Pro Val Ala Ile Arg Val Leu Asp
    450             455             460
Val Asn Asp Asn Ala Pro Lys Phe Ala Ala Pro Tyr Glu Gly Phe Ile
465             470             475                         480
Cys Glu Ser Asp Lys Leu Ser Asn Gln Pro Ile Val Thr Ser Ala Asp
            485             490             495
Asp Asp Asp Thr Ala Asn Gly Pro Arg Phe Ile Phe Ser Leu Pro Pro
        500             505             510
Glu Ile His Asn Pro Asn Phe Thr Val Arg Asp Asn Arg Asp Asn Thr
        515             520             525
Ala Gly Val Tyr Ala Arg Arg Gly Gly Phe Ser Arg Gln Lys Gln Asp
    530             535             540
Tyr Leu Leu Pro Ile Val Ile Ser Asp Gly Gly Ile Pro Pro Met Ser
545             550             555                         560
Ser Thr Asn Thr Leu Thr Ile Lys Val Cys Gly Cys Asp Val Asn Gly
            565             570             575
Ala Leu Leu Ser Cys Asn Ala Glu Ala Tyr Ile Leu Asn Ala Gly Leu
            580             585             590
Ser Thr Gly Ala Leu Ile Ala Ile Leu Ala Cys Ile Val Ile Leu Leu
        595             600             605
Leu Leu Gln Met Phe Ile Ser
610             615
```